United States Patent
Shin et al.

(10) Patent No.: US 12,235,523 B2
(45) Date of Patent: Feb. 25, 2025

(54) DEVICE AND METHOD FOR CORRECTING USER'S VISION AND PERFORMING CALIBRATION

(71) Applicant: SAMSUNG ELECTRONICS CO., LTD., Suwon-si (KR)

(72) Inventors: Sunghwan Shin, Suwon-si (KR); Jaewoo Ko, Suwon-si (KR); Bonkon Koo, Suwon-si (KR); Doyoun Kim, Suwon-si (KR); Sangho Yoon, Suwon-si (KR); Kyookeun Lee, Suwon-si (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 694 days.

(21) Appl. No.: 17/436,465

(22) PCT Filed: Jun. 28, 2021

(86) PCT No.: PCT/KR2021/008107
§ 371 (c)(1),
(2) Date: Sep. 3, 2021

(87) PCT Pub. No.: WO2022/010152
PCT Pub. Date: Jan. 13, 2022

(65) Prior Publication Data
US 2023/0176401 A1 Jun. 8, 2023

(30) Foreign Application Priority Data

Jul. 7, 2020 (KR) .................. 10-2020-0083464
Aug. 27, 2020 (KR) .................. 10-2020-0108795

(51) Int. Cl.
*A61B 3/02* (2006.01)
*A61B 3/032* (2006.01)
(Continued)

(52) U.S. Cl.
CPC .............. *G02C 7/083* (2013.01); *A61B 3/032* (2013.01); *G02B 27/0093* (2013.01);
(Continued)

(58) Field of Classification Search
CPC ........... A61B 3/103; A61B 3/14; A61B 3/113; A61B 3/125; A61B 3/024; A61B 3/1015;
(Continued)

(56) References Cited

U.S. PATENT DOCUMENTS 8,333,475 B2   12/2012   Sugio et al.
10,025,060 B2   7/2018   Lanman et al.
(Continued)

FOREIGN PATENT DOCUMENTS

KR   10-2016-0071139 A   6/2016
KR   10-1650706 B1   9/2016
(Continued)

OTHER PUBLICATIONS

Communication dated Oct. 13, 2021 issued by the International Searching Authority in counterpart Application No. PCT/KR2021/008107 (PCT/ISA/220, PCT/ISA/210, and PCT/ISA/237).

*Primary Examiner* — Dawayne Pinkney
(74) *Attorney, Agent, or Firm* — Sughrue Mion, PLLC

(57) ABSTRACT

Provided are a device and method for correcting the vision of a user and performing calibration. A method, performed by an augmented reality device, of performing gaze tracking sensor calibration based on a gaze of a user includes outputting at least one first character in a preset size through a waveguide of the augmented reality device, obtaining at least one first input for the at least one first character, obtaining at least one piece of first gaze information detected through a gaze tracking sensor of the augmented reality device at a time point at which the at least one first input is obtained, comparing the at least one first character with the at least one first input, and determining a first refractive power to be a refractive power of the varifocal lens of the augmented reality device, based on a result of the comparing.

13 Claims, 11 Drawing Sheets

(51) Int. Cl.

| | | |
|---|---|---|
| *A61B 3/10* | (2006.01) | |
| *A61F 9/02* | (2006.01) | |
| *G02B 27/00* | (2006.01) | |
| *G02B 27/01* | (2006.01) | |
| *G02C 7/08* | (2006.01) | |
| *G02F 1/29* | (2006.01) | |
| *G06F 3/01* | (2006.01) | |

(52) U.S. Cl.
CPC ......... *G02B 27/0172* (2013.01); *G02F 1/294* (2021.01); *G06F 3/013* (2013.01); *G02B 2027/0178* (2013.01)

(58) Field of Classification Search
CPC ... G02C 5/00; G02C 7/02; G02C 7/04; G02C 7/00; G02B 3/12
USPC ....... 351/239, 200, 205, 206, 210, 219, 222, 351/246, 41, 160 R, 161, 176, 159.01, 351/159.02, 159.34
See application file for complete search history.

(56) References Cited

U.S. PATENT DOCUMENTS

| | | | |
|---|---|---|---|
| 10,036,901 B2 | 7/2018 | Yadin et al. | |
| 10,242,501 B1* | 3/2019 | Pusch | H04N 21/44218 |
| 10,338,410 B1 | 7/2019 | Richards | |
| 10,345,590 B2 | 7/2019 | Samec et al. | |
| 10,386,638 B2 | 8/2019 | Kim et al. | |
| 10,855,977 B2 | 12/2020 | Perreault et al. | |
| 11,022,797 B2 | 6/2021 | Samec et al. | |
| 11,768,376 B1* | 9/2023 | Pedder | G02B 27/0179 |
| | | | 345/694 |
| 2012/0308972 A1* | 12/2012 | Miller | G06F 3/048 |
| | | | 434/236 |
| 2014/0361971 A1* | 12/2014 | Sala | G06F 3/013 |
| | | | 345/156 |
| 2016/0225012 A1* | 8/2016 | Ha | G06Q 30/0277 |
| 2017/0000329 A1* | 1/2017 | Samec | A61B 3/102 |
| 2017/0068134 A1 | 3/2017 | Yadin et al. | |
| 2017/0160440 A1 | 6/2017 | Yadin et al. | |
| 2017/0344111 A1 | 11/2017 | Kim | |
| 2021/0231973 A1 | 7/2021 | Macnamara et al. | |

FOREIGN PATENT DOCUMENTS

| | | |
|---|---|---|
| KR | 10-2017-0037692 A | 4/2017 |
| KR | 10-2017-0137726 A | 12/2017 |
| KR | 10-1880386 B1 | 7/2018 |
| KR | 10-1922343 B1 | 11/2018 |
| KR | 10-2019-0029727 A | 3/2019 |
| KR | 10-2019-0108909 A | 9/2019 |
| KR | 10-2038379 B1 | 10/2019 |
| KR | 10-2019-0131021 A | 11/2019 |
| KR | 10-2020-0063789 A | 6/2020 |
| WO | 2017/158486 A1 | 9/2017 |
| WO | 2017/182906 A1 | 10/2017 |
| WO | 2017/216716 A1 | 12/2017 |

* cited by examiner

DEVICE AND METHOD FOR CORRECTING USER'S VISION AND PERFORMING CALIBRATION

This application is a National Stage of International Application No. PCT/KR2021/008107, filed Jun. 28, 2021, which is based on and claims priority to Korean Patent Application No. 10-2020-0083464 filed Jul. 7, 2020 and Korean Patent Application No. 10-2020-0108795 filed Aug. 27, 2020, in the Korean Intellectual Property Office, the disclosures of which are incorporated by references herein in their entirety.

TECHNICAL FIELD

The disclosure relates to a device and method for correcting a user's vision and performing calibration, and more particularly, to a device and method for simultaneously performing vision correction and calibration of gaze tracking sensors with respect to a user.

BACKGROUND ART

Augmented reality is a technology that overlays a virtual image on a physical environment space of the real world or a real-world object, such that a user perceives the virtual image together with the physical environment space or the object in the real world. For example, an augmented reality device, which may be worn on a user's face (i.e., glasses) or head (i.e., head mount device (HMD)), allows the user to see a real scene and a virtual image together through a see-through waveguide in front of the eyes of the user. Recently, as research on such augmented reality devices is being actively conducted, various types of wearable devices have been released or they are expected to be released.

Augmented reality device users who wear glasses for vision correction in their daily lives need to use an additional tool, such as a corrective lens clip, when using an augmented reality device. However, because of the inconvenience of the corrective lens clip, augmented reality devices that use a varifocal lens to provide a vision correction function for users who need vision correction are being studied.

Meanwhile, glasses-type augmented reality devices need to be provided with a calibration process for a gaze tracking sensor, in order to track the user's gaze and accurately determine a gaze direction of the user by using the gaze tracking sensor. To this end, the augmented reality devices need to display a virtual image showing a plurality of points at a plurality of preset positions through a waveguide, and obtain the user's gaze information with respect to the plurality of points.

Accordingly, there is a need for a technology for determining the refractive power of a varifocal lens for correcting a user's vision and efficiently calibrating a gaze tracking sensor.

DISCLOSURE

Technical Problem

The disclosure provides an augmented reality device for performing determination of a refractive power of a varifocal lens for correcting the vision of a user by using a character in a preset size, while performing, at the same time, calibration of a gaze tracking sensor to track a gaze of the user, and a method thereof.

Moreover, the disclosure provides an augmented reality device for applying a refractive power of a varifocal lens of the augmented reality device that is determined in a gaze tracking sensor calibration process, thereby correcting the vision of a user, and a method thereof.

Also, the disclosure provides an augmented reality device capable of measuring a visual acuity of the user and performing gaze tracking sensor calibration, and a method thereof.

Additional aspects will be set forth in part in the description which follows and, in part, will be apparent from the description, or may be learned by practice of the presented embodiments of the disclosure.

Technical Solution

According to an aspect of the disclosure, there is provided a method of adjusting refractive power of a varifocal lens of an augmented reality device, the method comprising: outputting a first character having a first size through a waveguide of the augmented reality device; obtaining a first input response corresponding to the first character from a user; obtaining at least one piece of first gaze information detected through a gaze tracking sensor of the augmented reality device based on the first input response; comparing the first character with the first input response; and determining a first refractive power to be a refractive power of the varifocal lens of the augmented reality device, based on a result of the comparing.

According to another aspect of the disclosure, there is provided a non-transitory computer-readable recording medium having recorded thereon a program for executing the method on a computer.

According to another aspect of the disclosure, there is provided an augmented reality device comprising: a display; a gaze tracking sensor configured to track a gaze of a user; a varifocal lens; a memory storing one or more instructions; and a processor configured to execute the one or more instructions to: control the display to output a first character in having a first size, obtain a first input response corresponding to the first character from a user, control the gaze tracking sensor to obtain at least one piece of first gaze information detected through the gaze tracking sensor based on the first input response, compare the first character with the first input response, and determine a first refractive power to be a refractive power of the varifocal lens, based on a result of the compare operation.

DESCRIPTION OF DRAWINGS

The above and other aspects, features, and advantages of certain embodiments of the disclosure will be more apparent from the following description taken in conjunction with the accompanying drawings, in which.

MODE FOR DISCLOSURE

Figure 1A:
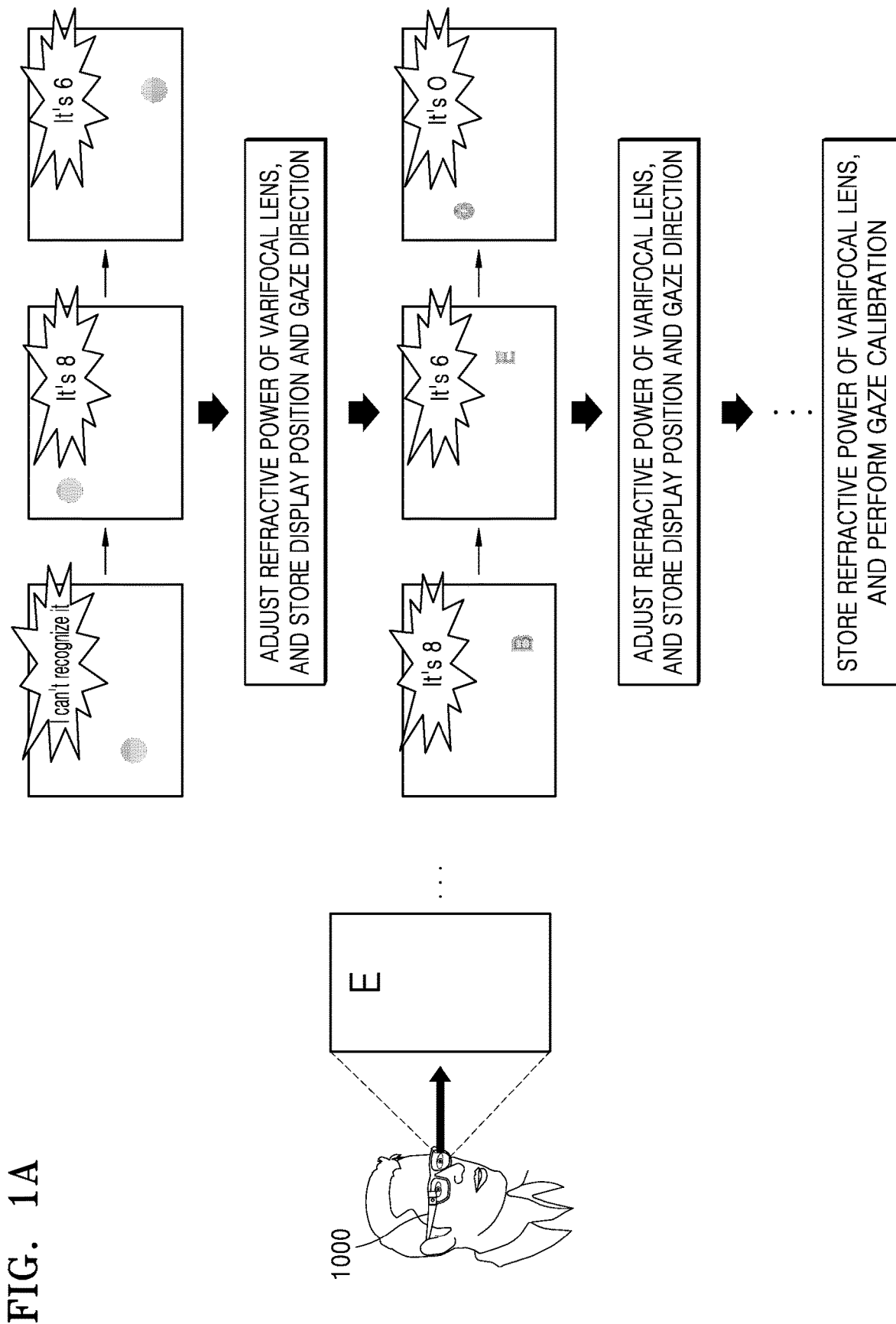
FIG. 1A is a diagram illustrating an example in which an augmented reality device determines a refractive power of a varifocal lens for correction of a user's vision, while performing gaze tracking sensor calibration for detecting a gaze of the user, according to an embodiment of the disclosure.

Hereinafter, embodiments of the present disclosure will be described in detail with reference to the accompanying drawings. In describing the embodiments of the present disclosure below, matters shown in the accompanying drawings are referred to and in the drawings, the same reference numbers or signs refer to components that perform substantially the same function. In the embodiments of the present disclosure, at least one of a plurality of elements refers to not only all of the plurality of elements, but also each one or all combinations thereof excluding the rest of the plurality of elements.

The disclosure may, however, be embodied in many different forms and should not be construed as being limited to the embodiments of the disclosure set forth herein. In order to clearly describe the disclosure, portions that are not relevant to the description of the disclosure are omitted, and similar reference numerals are assigned to similar elements throughout the present specification.

Throughout the disclosure, the expression "at least one of a, b or c" indicates only a, only b, only c, both a and b, both a and c, both b and c, all of a, b, and c, or variations thereof.

Throughout the disclosure, it will be understood that when an element is referred to as being "connected to" another element, it may be "directly connected to" the other element or be "electrically connected to" the other element through an intervening element. In addition, when an element is referred to as "including" a constituent element, other constituent elements may be further included not excluded unless there is any other particular mention on it.

The term 'augmented reality' (AR) herein may refer to a technology that provides viewing of a virtual image on a physical environment space of the real world or viewing of a virtual image together with a real object (i.e., a real world object).

In addition, the term 'augmented reality device' may refer to a device capable of creating 'augmented reality', and includes not only augmented reality glasses resembling eyeglasses that are typically worn on a user's face but also head-mounted display (HMD) apparatuses and augmented reality helmets that are worn on the user's head, or the like.

Meanwhile, the term 'real scene' may refer to a scene of the real world that the user sees through the augmented reality device, and may include a real-world object. In addition, the term 'virtual image' denotes an image generated by an optical engine, and may include both a static image and a dynamic image. The virtual image may be observed with a real scene, and may be an image representing information about a real object in the real scene, information about an operation of the augmented reality device, a control menu, or the like.

Accordingly, an augmented reality device according to one or more embodiment of the disclosure may be equipped with an optical engine to generate a virtual image using light generated by a light source, and a waveguide formed of a transparent material to guide the virtual image generated by the optical engine to the user's eyes and allow the user to see a scene of the real world together with the virtual image. As described above, the augmented reality device needs to be able to allow the user to observe a scene of the real world as well, and thus, an optical element for redirecting the path of light that basically has straightness is required in order to guide the light generated by the optical engine to the user' eyes through the waveguide. Here, the path of the light may be redirected by using reflection by, for example, a mirror, or by using diffraction by a diffractive element, for example, a diffractive optical element (DOE) or a holographic optical element (HOE), but the disclosure is not limited thereto.

In addition, gaze tracking sensor calibration herein may be an operation for obtaining gaze tracking sensor data according to a gaze direction of the user, based on the sizes and positions of eyes, interpupillary distance, or the like, that vary from user to user. According to another embodiment, the gaze tracking sensor calibration may be an operation of performing configuration for accurate determination of a position on the waveguide of the augmented reality device at which the user is looking, and may include, for example, an operation of mapping gaze information related to a gaze direction from the pupils of the user, with coordinate values representing a specific position on the waveguide of the augmented reality device. By performing the gaze tracking sensor calibration, a point on the waveguide at which the user is actually looking, and a point on the waveguide that the augmented reality device recognizes that the user is looking at, may be identical to each other.

Throughout the disclosure, a refractive index may refer to a degree to which a luminous flux is reduced in a medium as compared to a vacuum.

Throughout the disclosure, a refractive power may refer to a force that redirects a direction of a ray of light or a light path by a curved surface of a lens. The refractive power is the inverse of a focal length, and the unit of the refractive power is m−1 or diopter (D). The sign of the refractive power is positive (+) in a case of a convex lens and negative (−) in a case of a concave lens.

In addition, throughout the disclosure, the gaze information of the user may be information related to a gaze of the user, and may include, for example, positions of the pupils of the user, coordinates of the centers of the pupils, positions of the irises of the user, a gaze direction of the user, or the like.

Hereinafter, the disclosure will be described in detail with reference to the accompanying drawings.

Figure 1B:
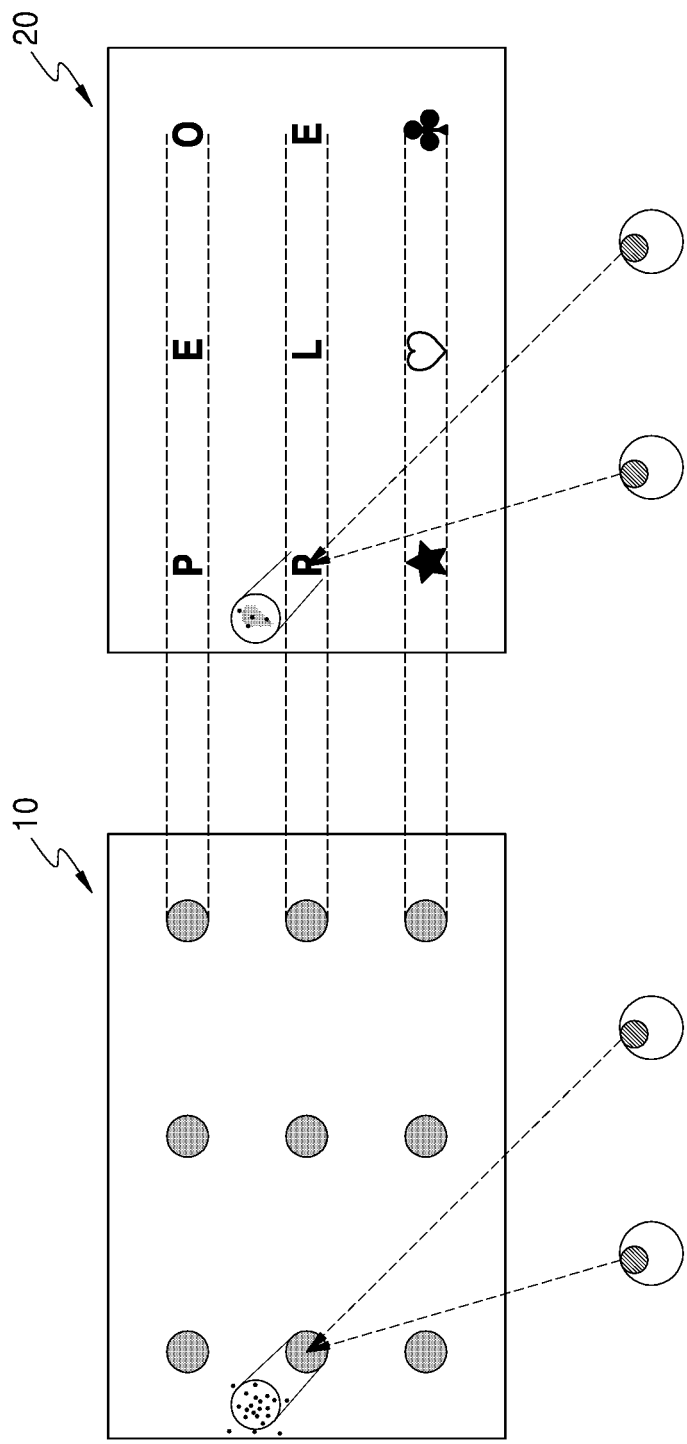
FIG. 1B is a diagram for comparing gaze tracking sensor calibration according to an embodiment of the disclosure, with a related art gaze tracking sensor calibration.

FIG. 1A is a diagram illustrating an example in which an augmented reality device 1000 determines a refractive power of a varifocal lens for correction of vision of a user, while performing gaze tracking sensor calibration for detecting a gaze of the user, according to an embodiment of the disclosure. FIG. 1B is a diagram comparing a gaze tracking sensor calibration 20 according to an embodiment of the disclosure, with a related art gaze tracking sensor calibration 10.

Referring to FIG. 1A, the augmented reality device 1000 may set sizes of characters used for determining the refractive power of the varifocal lens with respect to the user. According to an embodiment, the augmented reality device 1000 may set the size of the characters small enough to be also used as targets for the gaze tracking sensor calibration, thereby performing the gaze tracking sensor calibration at the same time as determining the refractive power of the varifocal lens with respect to the user.

The augmented reality device 1000 may display at least one character having a particular size, which may be a preset size, on a virtual vision measurement chart, receive at least one answer input by the user, and store a display position of each character for which the user input a correct answer, and a gaze direction and gaze information of the user detected by gaze tracking sensors when the at least one answer input by the user. According to an embodiment, the augmented reality device 1000 may store the gaze direction and the gaze information of the user detected by gaze tracking sensors each time the user inputs a correct answer. In order to perform the gaze tracking sensor calibration and the determination of the refractive power of the varifocal lens for the vision correction at the same time, the characters need to be displayed in sizes small enough to cause gaze points to be distributed within a small region, and accordingly, the augmented reality device 1000 may set the sizes of the characters to be displayed for determining the refractive power of the varifocal lens with respect to the user, to sizes required for performing the gaze tracking sensor calibration. The augmented reality device 1000 may adjust the refractive power of the varifocal lens of the augmented reality device 1000 based on whether the user input a correct answer for each displayed character, and may store a value (diopters) of the adjusted refractive power.

Referring to FIG. 1B, in a related art gaze tracking sensor calibration method 10, a plurality of points are displayed, and the gaze tracking sensor calibration is performed by using distribution of gaze points detected by gaze tracking sensors when it is determined that the user is looking at each of the plurality of points. On the other hand, in a gaze tracking sensor calibration method 20 of FIG. 1B according to an embodiment of the disclosure, characters in preset small sizes may be displayed on positions for the gaze tracking sensor calibration. Here, the sizes of the characters may be set to correspond to the sizes of the plurality of points displayed in the related art gaze tracking sensor calibration method, so as to obtain a gaze point distribution. Accordingly, in a case of performing the gaze tracking sensor calibration according to an embodiment of the disclosure, the vision of the user may be measured by comparing the displayed characters with the answers input by the user while performing the gaze tracking sensor calibration, and because gazes of the user whose vision is being tested are focused on the characters, the calibration of the gaze tracking sensors may be performed more efficiently.

For example, referring to FIG. 1A, the augmented reality device 1000 may successively display a plurality of characters while successively receiving a response or answers input by the user, and may determine whether each of the response or the answers input by the user is correct. In this case, after the user inputs an incorrect answer, the augmented reality device 1000 may adjust the refractive power of the varifocal lens before displaying a next character. For example, in a case where the refractive power of the varifocal lens is −1.0 D, and the user input an incorrect answer for a first displayed character, the augmented reality device 1000 may adjust the refractive power of the varifocal lens to −2.0 D, and then display a second character.

According to another embodiment, for example, the augmented reality device 1000 may successively display the plurality of characters while successively receiving answers input by the user, and may adjust the refractive power of the varifocal lens of the augmented reality device 1000 based on a correct answer rate of the answers input by the user for the displayed characters. For example, in a case where the refractive power of the varifocal lens is −1.0 D, and the user input answers for first to third displayed characters, the augmented reality device 1000 may adjust the refractive power of the varifocal lens to −2.0 D based on a correct answer rate of the answers input by the user, and then display a fourth character.

In addition, after the refractive power of the varifocal lens is adjusted, the augmented reality device 1000 may display at least one character for vision measurement on the virtual vision measurement chart, receive at least one answer input by the user, and store a display position of each character for which the user input a correct answer, and a gaze direction of the user detected when the user is saying each correct answer. The augmented reality device 1000 may additionally adjust the refractive power of the varifocal lens of the augmented reality device 1000 based on the correct answer rate of the answers input by the user for the displayed characters, and may store the value of the adjusted refractive power. Also, the augmented reality device 1000 may perform the gaze tracking sensor calibration with respect to the user by using the stored display positions of characters and gaze directions, and may determine the refractive power of the varifocal lens for correcting the vision of the user.

The augmented reality device 1000 may perform vision measurement by using characters that are small enough to be used as targets for the gaze tracking sensor calibration, and may efficiently adjust the refractive power of the varifocal lens with respect to the user, based on whether each of the answers input by the user is correct.

The augmented reality device 1000 is a device capable of creating augmented reality, and may include, for example, augmented reality glasses resembling eyeglasses that are worn on the user's face, head-mounted display (HMD) apparatuses and augmented reality helmets that are worn on the user's head, or the like.

Figure 2:
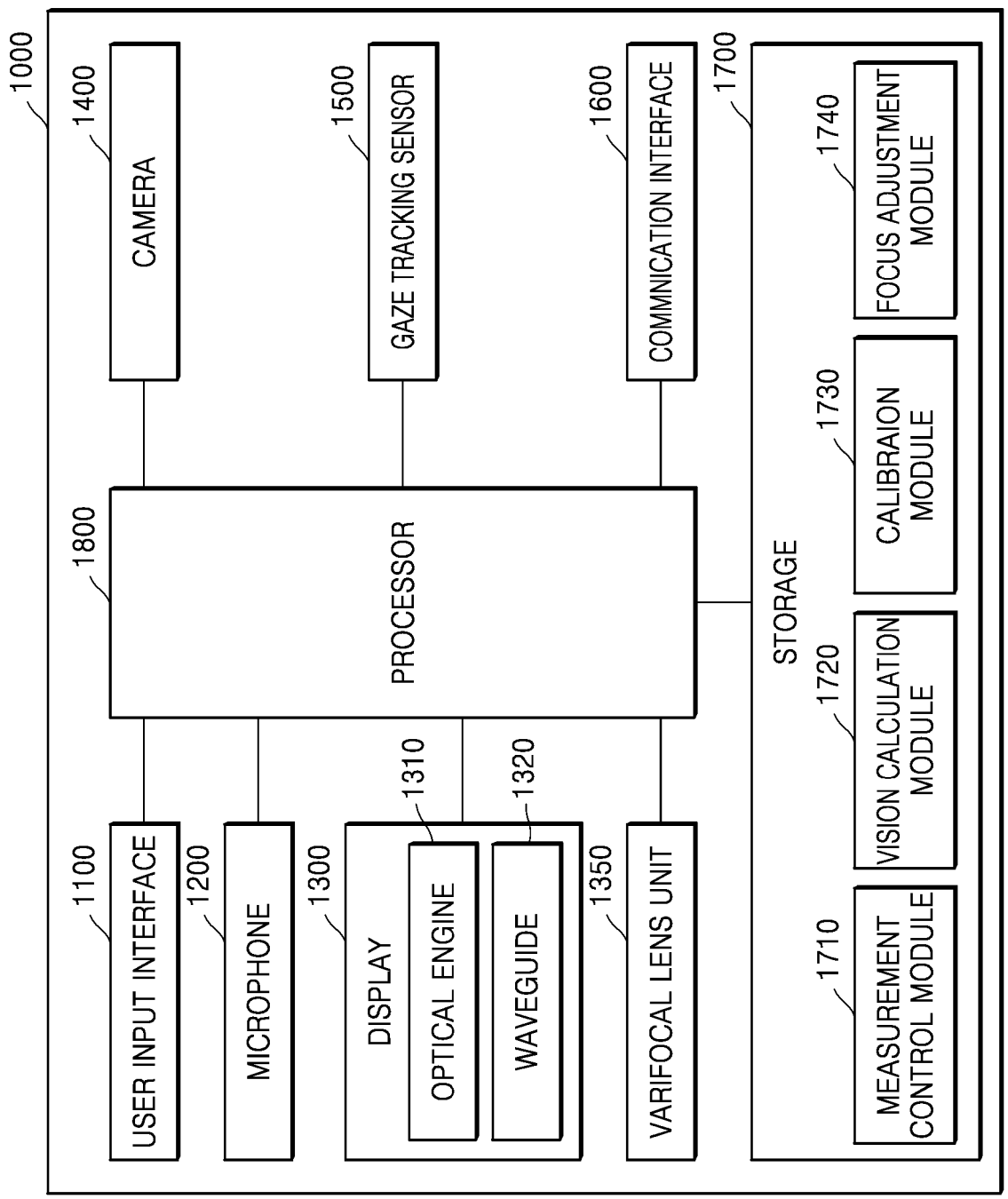
FIG. 2 is a block diagram of an augmented reality device, according to an embodiment of the disclosure.

FIG. 2 is a block diagram of the augmented reality device 1000, according to an embodiment of the disclosure.

Referring to FIG. 2, the augmented reality device 1000 according to an embodiment of the disclosure may include a user input interface 1100, microphone 1200, a display 1300, a varifocal lens unit 1350, a camera 1400, a gaze tracking sensor 1500, a communication interface 1600, a storage 1700, and a processor 1800. In addition, the display 1300 may include an optical engine 1310 and a waveguide 1320.

The user input interface 1100 may include components or devices through which the user inputs data for controlling the augmented reality device 1000. For example, the user input interface 1100 may include, but is not limited to, a key pad, a dome switch, a touch pad (e.g., a touch-type capacitive touch pad, a pressure-type resistive overlay touch pad, an infrared sensor-type touch pad, a surface acoustic wave conduction touch pad, an integration-type tension measurement touch pad, a piezoelectric effect-type touch pad), a jog wheel, a jog switch, or the like. According to an embodiment of the disclosure, the user input interface 1100 may receive a user input for measuring the vision of the user and performing the gaze tracking sensor calibration. The gaze tracking sensor calibration may be an operation of performing configuration for accurate determination of a position on the waveguide of the augmented reality device at which the user is looking, and may be, for example, an operation of correcting a mapping relationship between a gaze direction from the pupils of the user and a specific position on the waveguide of the augmented reality device.

The microphone 1200 may receive an external audio signal, and process the received audio signal into electrical voice data. For example, the microphone 1200 may receive an audio signal from an external device or a speaker. The microphone 1200 may perform various de-noising algorithms for removing noise generated when the external audio signal is being received. The microphone 1200 may receive a voice input of the user for controlling the augmented reality device 1000. The microphone 1200 may receive a voice input spoken by the user to identify the character displayed through the display 1300 that will be described below.

The display 1300 may display information processed by the augmented reality device 1000. For example, the display 1300 may display a user interface for capturing an image of surroundings of the augmented reality device 1000, and information related to a service provided based on the captured image of the surroundings of the augmented reality device 1000.

According to an embodiment of the disclosure, the display 1300 may be a display device configured to provide an augmented reality (AR) image. The display 1300 according to an embodiment of the disclosure may include the optical engine 1310 and the waveguide 1320. The optical engine 1310 may project, onto the waveguide 1320, light of a virtual image to be displayed. The optical engine 1310 may include a light source and an image panel. The light source may an optical element that illuminates the light and may generate the light by adjusting colors of RGB. The light source may be configured as, for example, a light emitting diode (LED). The image panel may be configured as a reflective image panel that modulates and reflects the light illuminated by the light source to light including a two-dimensional image. The reflective image panel may be, for example, a digital micromirror device (DMD) panel or a liquid crystal on silicon (LCoS) panel, or another type of reflective image panel capable of modulating and reflecting the light illuminated by the light source to light including a two-dimensional image.

The virtual image projected onto the waveguide 1320 may be reflected in the waveguide 1320 according to the principle of total reflection. The light path of the virtual image projected onto the waveguide 1320 may be redirected by diffraction gratings formed in a plurality of regions such that the virtual image is finally output to the user's eyes. The waveguide 1320 may perform functionality similar to a light guide plate that redirects the light path of the virtual image.

The waveguide 1320 may be formed of a transparent material such that the user wearing the device 1000 sees a partial region of the rear side of the waveguide 1320. The waveguide 1320 may be configured as a flat plate of a single layer or multi-layer structure made of a transparent material through which light may be reflected and propagated. The waveguide 1320 may face an output surface of the optical engine to receive the light of the projected virtual image. Here, the transparent material may include a material through which light may pass. According to an embodiment, the transparency may not be 100% and the transparent material may have a certain color. According to an embodiment of the disclosure, the waveguide 1320 is formed of the transparent material, thus the user may view not only a virtual object of the virtual image totally reflected through the waveguide 1320 but also an external real scene, and accordingly, the waveguide 1320 may be referred to as a see-through display. The display 1300 may provide an augmented reality image by outputting the virtual image through the waveguide 1320.

The varifocal lens unit 1350 may be mounted on the augmented reality device 1000 for correcting the vision of the user. According to an embodiment, the varifocal lens unit 1350 may be arranged to overlap the waveguide 1320 so as to face the user's eyes. However, the disclosure is not limited thereto, and the varifocal lens unit 1350 may be arranged in a different manner with respect to the waveguide. In general, the varifocal lens unit 1350 may be implemented as a liquid lens or a liquid crystal lens, and may be implemented as, for example, a liquid lens in which a flexible plastic membrane is surrounding a transparent fluid. An electrical signal applied to the varifocal lens unit 1350 may cause the fluid in the varifocal lens unit 1350 to move, and thus, the refractive power of the varifocal lens unit 1350 may be adjusted. As another example, the varifocal lens unit 1350 may be implemented as a liquid crystal lens in which transparent electrodes are arranged at both sides of a transparent liquid crystal layer. An electrical signal applied to the transparent electrodes may cause the arrangement of liquid crystals in the liquid crystal layer to be changed, thus, the path of light passing through the varifocal lens may be redirected, and accordingly, the refractive power of the varifocal lens unit 1350 may be adjusted. For example, electrical signals or values of voltages to be applied to the electrodes may correspond to diopter values (e.g., . . . , −3D, −2D, −1D, 0, 1D, 2D, 3D, . . . ) to which the refractive power of the varifocal lens unit 1350 is to be adjusted, and when the electrical signal or the voltage is applied to the electrodes, a refractive power of the corresponding diopter value may be applied to the varifocal lens unit 1350. However, the disclosure is not limited thereto, and according to another embodiment, the electrical signals or the values of the voltages to be applied to the electrodes may be preset such that the refractive power of the varifocal lens unit 1350 may be adjusted to a continuous value. In general, as the refractive power of a lens increases, the focal length of the lens may decrease. In a case of the augmented reality device 1000 being a glasses-type device, the varifocal lens unit 1350 may include a left varifocal lens and a right varifocal lens.

The camera 1400 may capture an image of the surroundings of the augmented reality device 1000. In a case where an application that requires an image capturing function is executed, the camera 1400 may obtain an image frame such as a still image or a moving image, through an image sensor. An image captured by the image sensor may be processed by the processor 1800 or a separate image processor. The camera 1400 may include, for example, but is not limited to, at least one of a rotatable RGB camera or a plurality of depth camera modules.

The gaze tracking sensor 1500 may track a gaze of the user wearing the augmented reality device 1000. The gaze tracking sensor 1500 may be arranged to face the eyes of the user, and may detect a gaze direction of the left eye of the user and a gaze direction of the right eye of the user. The detection of the gaze direction of the user may include an operation of obtaining gaze information related to a gaze of the user.

The gaze tracking sensor 1500 may include, for example, at least one of an infrared (IR) scanner or an image sensor, and in a case of the augmented reality device 1000 being a glasses-type device, a plurality of gaze tracking sensors may be arranged around a left waveguide 1320L and a right waveguide 1320R of the augmented reality device 1000 to face the eyes of the user.

The gaze tracking sensor 1500 may detect data related to gazes of the eyes of the user. The gaze information of the user may be generated based on the data related to the gazes of the eyes of the user. The gaze information may be information related to a gaze of the user, and may include, for example, information about positions of the pupils of the user, coordinates of the centers of the pupils, a gaze direction of the user, or the like. The gaze direction of the user may be a direction from the center of the pupil of the user to a position at which the user is looking.

The gaze tracking sensor 1500 may provide light to an eye (the left or right eye) of the user, and detect the amount of light reflected from the eye of the user. For instance, the gaze tracking sensor 1500 may emit light to a left eye or a right eye of the user, and detect the amount of light reflected from the eye of the user. In addition, based on the detected amount of the light, a gaze direction of the eye of the user, a position of the pupil of the eye of the user, coordinates of the center of the pupil, or the like may be detected.

According to another embodiment, the gaze tracking sensor 1500 may provide light to an eye of the user, and capture an image of the eye. In addition, based on the capture image of the eye of the user, a gaze direction of the eye of the user, a position of the pupil of the eye of the user, coordinates of the center of the pupil, or the like may be detected.

According to an embodiment of the disclosure, the gaze tracking sensor 1500 may sense the eyes of the user wearing the augmented reality device 1000 at every preset time interval. According to an embodiment of the disclosure, the gaze tracking sensor 1500 may sense the eyes of the user wearing the augmented reality device 1000 periodically. According to another embodiment of the disclosure, the gaze tracking sensor 1500 may sense the eyes of the user wearing the augmented reality device 1000 aperiodically.

According to an example embodiment, the communication interface 1600 may transmit data to an external device or a server, and the communication interface receive data from the external device or the server. According to an embodiment, the data may be related to a service based on an image obtained by capturing the surroundings of the augmented reality device 1000.

The storage 1700 may store a program to be executed by the process that will be described below, and may store data input to or output from the augmented reality device 1000.

The storage 1700 may include at least one type of storage medium of a flash memory type, a hard disk type, a multimedia card micro type, a card type memory (for example, SD or XD memory), random access memory (RAM), a static random access memory (SRAM), read only memory (ROM), electrically erasable programmable read-only memory (EEPROM), programmable read-only memory (PROM), a magnetic memory, a magnetic disk, or an optical disk.

According to an embodiment, programs, codes or instructions stored in the storage 1700 may be classified into a plurality of modules according to their functions, for example, into a measurement control module 1710, a vision calculation module 1720, a calibration module 1730, and a focus adjustment module 1740.

The processor 1800 may control the overall operation of the augmented reality device 1000. For example, the processor 1800 may generally control the user input interface 1100, the microphone 1200, the display 1300, the varifocal lens unit 1350, the camera 1400, the gaze tracking sensor 1500, the communication interface 1600, and the storage 1700, by executing programs stored in the storage 1700.

According to an embodiment, the processor 1800 may execute the measurement control module 1710, and by executing the measurement control module 1710 stored in the storage 1700, the processor 1800 may adjust the refractive power of the varifocal lens unit 1350 of the augmented reality device 1000 to correct the vision of the user, while performing the gaze tracking sensor calibration for tracking a gaze of the user.

According to an embodiment, by executing the measurement control module 1710, the processor 1800 may successively display, on the waveguide 1320 of the display 1300, at least one character for determining the refractive power of the varifocal lens unit 1350, and successively receive at least one answer input by the user by saying a phrase to identify the character being displayed.

In order to determine the refractive power of the varifocal lens unit 1350 with respect to the user, and perform the gaze tracking sensor calibration, the processor 1800 may successively display at least one first character in a certain size corresponding to a preset corrected visual acuity, at one or more first positions on the waveguide 1320 of the display 1300, and successively receive at least one input response from the user. According to an embodiment, the processor 1800 may receive a voice input from the user with respect to the at least one first character being displayed. The first character may be in a size small enough to cause gaze points to be distributed within a small region, in order to perform the gaze tracking sensor calibration. For example, the first character may be in a size corresponding to a visual acuity of 1.0, such that a corrected visual acuity of the user is to be 1.0. The corrected visual acuity may be the visual acuity of the user wearing a lens to which a certain refractive power is applied. For example, the processor 1800 may cause the at least one first character in a size corresponding to the corrected visual acuity to be displayed at a preset depth for measuring the visual acuity of the user, in a random order. The augmented reality device 1000 may adjust the refractive power of the varifocal lens unit 1350 so as to correct the visual acuity of the user to be 1.0, and to this end, may set the size and the depth of the first character to measure a visual acuity of 1.0. For example, the augmented reality device 1000 may cause the first character in a preset size to be displayed at a preset depth for measuring a visual acuity, and accordingly, the augmented reality device 1000 may allow the user to observe the first character in the preset size displayed at the preset depth.

The processor 1800 may adjust the refractive power of the varifocal lens unit 1350 so as to correct the visual acuity of the user wearing the augmented reality device 1000 to be 1.0, while executing operations for performing the gaze tracking sensor calibration. For example, the processor 1800 may display a first character 'A' in a size corresponding to a visual acuity of 1.0 at one of a plurality of first positions on the waveguide 1320, receive a first voice input spoken by the user to identify the first character 'A', then display another first character '1' in a size corresponding to a visual acuity of 1.0 at another one of the plurality of first positions on the waveguide 1320, and receive another first voice input spoken by the user to identify the another first character '1'. In addition, the processor 1800 may successively further display other first characters on the waveguide 1320, and successively receive first voice inputs of the user for the other first characters being displayed. In this case, the processor 1300 may determine depth values of the first characters 'A' and '1', such that the first characters 'A' and '1' may be displayed at a preset vision measurement distance. The vision measurement distance may be a distance for measuring the vision of the user, and may be a distance between the eyes of the user and the virtual vision measurement chart.

In this case, the first positions at which the first characters are displayed may be determined such that various gaze directions of the user may be stored with respect to a plurality of display positions on the waveguide 1320 for the gaze tracking sensor calibration. For example, preset positions on the waveguide 1320 that are required for the gaze tracking sensor calibration may be successively selected as the first positions at which the first characters are displayed. The positions required for the augmented reality device 1000 to perform the gaze tracking sensor calibration with respect to the user may be preset when the augmented reality device 1000 is manufactured, but the disclosure is not limited thereto.

According to an embodiment of the disclosure, the processor 1800 may track a gaze direction of the user by controlling the gaze tracking sensor 1500. The processor 1800 may detect at least one piece of first gaze information of the user through the gaze tracking sensor 1500, when receiving at least one first voice input. The processor 1800 may detect the first gaze information of the user at a time point at which the first voice input of the user for the first character displayed on the waveguide 1320 is received. For example, the processor 1800 may continuously detect the gaze information of the user through the gaze tracking sensor 1500, and, when the reception of the first voice input of the user through the microphone 1200 is detected, may obtain a first gaze direction by using the gaze information of the user detected upon the reception of the first voice input. In this case, for example, as the character for the gaze tracking sensor calibration is displayed on the waveguide 1320, an operation of monitoring gaze directions of the user may be started, but the disclosure is not limited thereto.

A gaze direction of the user at a time point at which a voice input is received may be, for example, but is not limited to, a gaze direction during a preset critical time period before and after a time point at which the reception of the voice input is detected through the microphone 1200.

According to an embodiment, by executing the measurement control module 1710, the processor 1800 may compare the at least one first character displayed on the waveguide 1320 with at least one character corresponding to the at least one first voice input spoken by the user to identify the at least one first character. The processor 1800 may identify, from the first voice input, a character corresponding to the first voice input by using a speech-to-text (STT) function. For example, the processor 1800 may determine whether a plurality of first characters are identical to characters corresponding to first voice inputs spoken by the user to identify the plurality of first characters, respectively. In addition, the processor 1800 may calculate a first correct answer rate indicating how many characters corresponding to the first voice inputs spoken by the user to identify the plurality of first characters are identical to the plurality of first characters, respectively.

In a case of the first correct answer rate being greater than or equal to a preset threshold, the processor 1800 may store the first gaze direction detected when each of the first voice inputs that are correct is received, together with the display position of the first character corresponding to each of the first voice inputs that are correct. The stored first gaze directions and the stored display positions of the first characters may be used for the gaze tracking sensor calibration with respect to the user. On the other hand, in a case of the first correct answer rate being lower than the preset threshold, the processor 1800 may ignore the detected first gaze directions Although it is described above that the first gaze directions are ignored in a case of the first correct answer rate being lower than the preset threshold, the disclosure is not limited thereto. For example, according to another embodiment, even in a case of the first correct answer rate being lower than the preset threshold, the first gaze directions may be used for the gaze tracking sensor calibration.

According to another embodiment, for example, the processor 1800 may display a single first character, and determine whether a character corresponding to a first voice input spoken by the user to identify the displayed first character is identical to the first character. Here, in a case of the first voice input of the user being correct, the processor 1800 may store a first gaze direction detected when the first voice input that is correct is received, together with the display position of the first character corresponding to the first voice input that is correct. Although it is described above that the first gaze direction is stored together with the display position of the first character corresponding to the first voice input only in a case of the first voice input of the user being correct, the disclosure is not limited thereto. Even in a case of the first voice input being incorrect, the first gaze direction may be stored together with the display position of the first character corresponding to the first voice input that is incorrect.

According to an embodiment of the disclosure, the processor 1800 may execute the focus adjustment module 1740, and by executing the focus adjustment module 1740, the processor 1800 may adjust the refractive power of the varifocal lens unit 1350. According to an embodiment of the disclosure, by executing the focus adjustment module 1740, the processor 1800 may apply an electrical signal to the varifocal lens unit 1350, and the refractive power of the varifocal lens unit 1350 may be adjusted by the applied electrical signal.

The processor 1800 may adjust the refractive power of the varifocal lens unit 1350 to a first refractive power based on the first correct answer rate. For example, in a case of the first correct answer rate being low, the refractive power of the varifocal lens unit 1350 may be adjusted by a large amount, whereas in a case of the first correct answer rate being high, the refractive power of the varifocal lens unit 1350 may be adjusted by a small amount. Here, the refractive power being adjusted by a large amount means that the change in the diopter value is large, whereas the refractive power being adjusted by a small amount means that the change in the diopter value is small. In addition, for example, the processor 1800 may adjust the refractive power of the varifocal lens unit 1350 considering the visual acuity of the user. In addition, in a case of the first correct answer rate being greater than the preset threshold, the processor 1800 may determine and store the refractive power with respect to the user, to be the current refractive power of the varifocal lens unit 1350.

According to another embodiment, for example, the processor 1800 may display a single first character, and, in a case of a first voice input of the user for the first character being incorrect, may adjust the refractive power of the varifocal lens unit 1350. In addition, for example, in a case of the first voice input of the user for the first character being correct, the processor 1800 may determine and store the refractive power with respect to the user, to be the current refractive power of the varifocal lens unit 1350.

According to an embodiment of the disclosure, after the refractive power of the varifocal lens unit 1350 is adjusted to the first refractive power, the processor 1800, by executing the measurement control module 1710, may successively display at least one second character at one or more second position on the waveguide 1320, and successively receive at least one second response input by the user with respect to the at least one second character displayed. According to an embodiment, the processor 1800 may receive voice input of the user for the at least one second character being displayed. The second character may be displayed on the waveguide 1320 in the same size and at the same depth as those of the first character. In addition, similar to the first position at which the first character is displayed, the second position at which the second character is displayed may be selected from among the positions required for the gaze tracking sensor calibration.

For example, the processor 1800 may successively display second characters that are in a certain size preset for determining the refractive power and performing the gaze tracking sensor calibration, and are randomly selected, at a preset depth for measuring the visual acuity of the user. For example, the processor 1800 may display a second character 'B' in a size corresponding to a visual acuity of 1.0 at one of a plurality of second positions on the waveguide 1320, receive a second voice input spoken by the user to identify the second character '13', then display a second character '2' in a size corresponding to a visual acuity of 1.0 at another one of the plurality of second positions on the waveguide 1320, and receive a second voice input spoken by the user to identify the second character '2'. In addition, the processor 1800 may successively further display other second characters on the waveguide 1320, and successively receive second voice inputs of the user for the other second characters being displayed.

In this case, the second positions at which the second characters are displayed may be determined such that various second gaze directions of the user may be obtained with respect to the plurality of display positions on the waveguide 1320 for the gaze tracking sensor calibration. The second position at which the second character is displayed by the processor 1800 may be a position from which it is determined that data for the gaze tracking sensor calibration is not sufficiently obtained, from among the positions on the waveguide 1320 required for the gaze tracking sensor calibration. For example, in a case where it is determined that a voice input spoken by the user to identify a character displayed at a specific position has been received a preset number of times, the processor 1800 may determine that the data for the gaze tracking sensor calibration has been sufficiently obtained, but the disclosure is not limited thereto.

In addition, for example, the processor 1800 may display the second characters preferentially at the second positions that do not correspond to the stored first gaze directions, from among the plurality of second positions on the waveguide 1320 for the gaze tracking sensor calibration.

According to an embodiment of the disclosure, the processor 1800 may detect a second gaze direction of the user when a second voice input is received, by controlling the gaze tracking sensor 1500. The processor 1800 may detect the second gaze direction of the user when the second voice input of the user for the second character being displayed on the waveguide 1320 is received through the microphone 1200. For example, the processor 1800 may monitor gaze directions of the user through the gaze tracking sensor 1500, and, when the reception of the second voice input of the user through the microphone 1200 is detected, may extract the second gaze direction at a time point at which the second voice input is received, from among monitored gaze directions. For example, the processor 1800 may monitor the gaze directions of the user by using the gaze tracking sensor 1500 including at least one of an IR scanner or an image sensor, so as to generate gaze information related to the gaze directions of the user. In this case, in order to monitor the gaze directions of the user, the processor 1800 may sense the eyes of the user wearing the augmented reality device 1000, for example, at preset time intervals, but the disclosure is not limited thereto. In addition, the processor 1800 may extract data indicating the second gaze direction at the time point at which the second voice input is received through the microphone 1200, from the gaze information related to the gaze directions of the user.

By executing the measurement control module 1710, the processor 1800 may compare the at least one second character displayed on the waveguide 1320 with at least one character corresponding to the at least one second voice input spoken by the user to identify the at least one second character.

For example, the processor 1800 may determine whether a plurality of second characters are identical to characters corresponding to second voice inputs spoken by the user to identify the plurality of second characters, respectively. In addition, the processor 1800 may calculate a second correct answer rate indicating how many characters corresponding to the second voice inputs spoken by the user to identify the plurality of second characters are identical to the plurality of second characters, respectively. In addition, for example, in a case of the second correct answer rate being greater than or equal to a preset threshold, the processor 1800 may store the second gaze direction detected when each of the second voice inputs that are correct is received, together with the display position of the second character corresponding to each of the second voice inputs that are correct. The stored second gaze directions and the stored display positions of the second characters may be used for the gaze tracking sensor calibration with respect to the user.

For example, the processor 1800 may determine whether the second character is identical to the character corresponding to the second voice input spoken by the user to identify the second character. In addition, for example, in a case of the second character being identical to the character corresponding to the second voice input spoken by the user to identify the second character, the processor 1800 may store the second gaze direction at the time point at which the second voice input is received, together with the display position of the second character, for the gaze tracking sensor calibration.

Although it is described above that the second gaze direction is stored together with the display position of the second character corresponding to the second voice input only in a case of the second voice input of the user being correct, the disclosure is not limited thereto. Even in a case of the second voice input being incorrect, the second gaze direction may be stored together with the display position of the second character corresponding to the second voice input that is incorrect.

By executing the focus adjustment module 1740, the processor 1800 may adjust the refractive power of the varifocal lens unit 1350 to a second refractive power. For example, in a case of the second correct answer rate being lower than or equal to a preset threshold, the refractive power of the varifocal lens unit 1350 may be adjusted by a large amount, whereas in a case of the second correct answer rate being greater than or equal to the preset threshold, the refractive power of the varifocal lens unit 1350 may be adjusted by a small amount. The refractive power being adjusted by a large amount means that the change in the diopter value of the varifocal lens unit 1350 is large, whereas the refractive power being adjusted by a small amount means that the change in the diopter value of the varifocal lens unit 1350 is small. In addition, for example, the processor 1800 may adjust the refractive power of the varifocal lens unit 1350 considering the visual acuity of the user.

According to another embodiment, for example, in order to adjust the refractive power of the varifocal lens unit 1350, the processor 1800 may display a single second character, and receive a second voice input spoken by the user to identify the second character being displayed. Here, in a case where the second character is not identical to a character corresponding to the second voice input spoken by the user to identify the second character, the processor 1800 may additionally adjust the refractive power of the varifocal lens unit 1350.

According to an embodiment of the disclosure, the processor 1800 may execute the vision calculation module 1720, and by executing the vision calculation module 1720, the processor 1800 may calculate the visual acuity of the user. The processor 1800 may determine the refractive power of the varifocal lens unit 1350. For example, in a case of the second correct answer rate being 90% or greater, the processor 1800 may determine the refractive power with respect to the user, to be the current refractive power of the varifocal lens unit 1350.

In a case where the second correct answer rate is not high enough to determine the refractive power of the varifocal lens unit 1350, the processor 1800 may repeat operations of adjusting the refractive power of the varifocal lens unit 1350, displaying characters, receiving voice inputs of the user, detecting gaze directions of the user, calculating a correct answer rate of the received voice inputs, and performing the gaze tracking sensor calibration.

According to another embodiment, for example, the processor 1800 may determine the refractive power of the varifocal lens unit 1350 with respect to the user, based on a user input for determining the refractive power.

In addition, the processor 1800 may identify a visual acuity of the user corresponding to the determined refractive power. In this case, the processor 1800 may identify the visual acuity of the user by using a table indicating visual acuities respectively corresponding to refractive powers of a lens. In general, the visual acuities and the refractive powers for vision correction correspond to each other as shown in Table 1 below, but are not limited thereto.

TABLE 1

| Uncorrected visual acuity | Refractive power (diopters) of varifocal lens |
|---|---|
| 0.05 | −6.0 |
| 0.1 | −3.0 |
| 0.15 | −2.5 |
| 0.2 | −2.0 |
| 0.3 | −1.5 |
| 0.4 | −1.25 |
| 0.5 | −1.0 |
| 0.6 | −0.75 |
| 0.7 | −0.5 |
| 0.8 | −0.5 |

According to an embodiment of the disclosure, the processor 1800 may execute the calibration module 1730, and by executing the calibration module 1730, the processor 1800 may perform the gaze tracking sensor calibration with respect to the user. For example, the processor 1800 may perform the gaze tracking sensor calibration with respect to the user by using gaze information related to the stored first gaze directions and the stored display positions of the first characters, and the stored second gaze directions and the stored display positions of the second characters. In this case, for example, the display positions and the gaze directions stored after the refractive power of the varifocal lens unit 1350 is adjusted may be preferentially used for the gaze tracking sensor calibration, but the disclosure is not limited thereto.

As the gaze tracking sensor calibration with respect to the user is performed, the gaze information related to the gaze directions of the user may be mapped with coordinate values representing positions on the waveguide 1320 at which the user was looking, into calibration values, and the calibration values may be stored. For example, the gaze information related to the gaze directions of the user may be mapped with the coordinate values representing positions at which the user was looking, into a table, and the table may be stored.

Accordingly, the augmented reality device 1000 may adjust the refractive power of the varifocal lens unit 1350 to correct the vision of the user, while efficiently performing the gaze tracking sensor calibration of the augmented reality device 1000 based on the gaze directions of the user precisely looking at the characters in a small size.

Meanwhile, according to an embodiment of the disclosure, before the vision correction and the gaze tracking sensor calibration with respect to the user are performed, the processor 1800 may receive a user input for inputting the visual acuity of the user. In this case, the processor 1800 may display, on the waveguide 1320, a graphical user interface (GUI) for receiving the visual acuity of the user. In this case, the processor 1800 may receive the visual acuity of the user through the GUI, and adjust the refractive power of the varifocal lens unit 1350 in advance based on the received visual acuity. After the refractive power of the varifocal lens unit 1350 is adjusted, the processor 1800 of the augmented reality device 1000 may perform the vision correction and the gaze tracking sensor calibration with respect to the user, while displaying the first or second character on the waveguide 1320.

Figure 3:
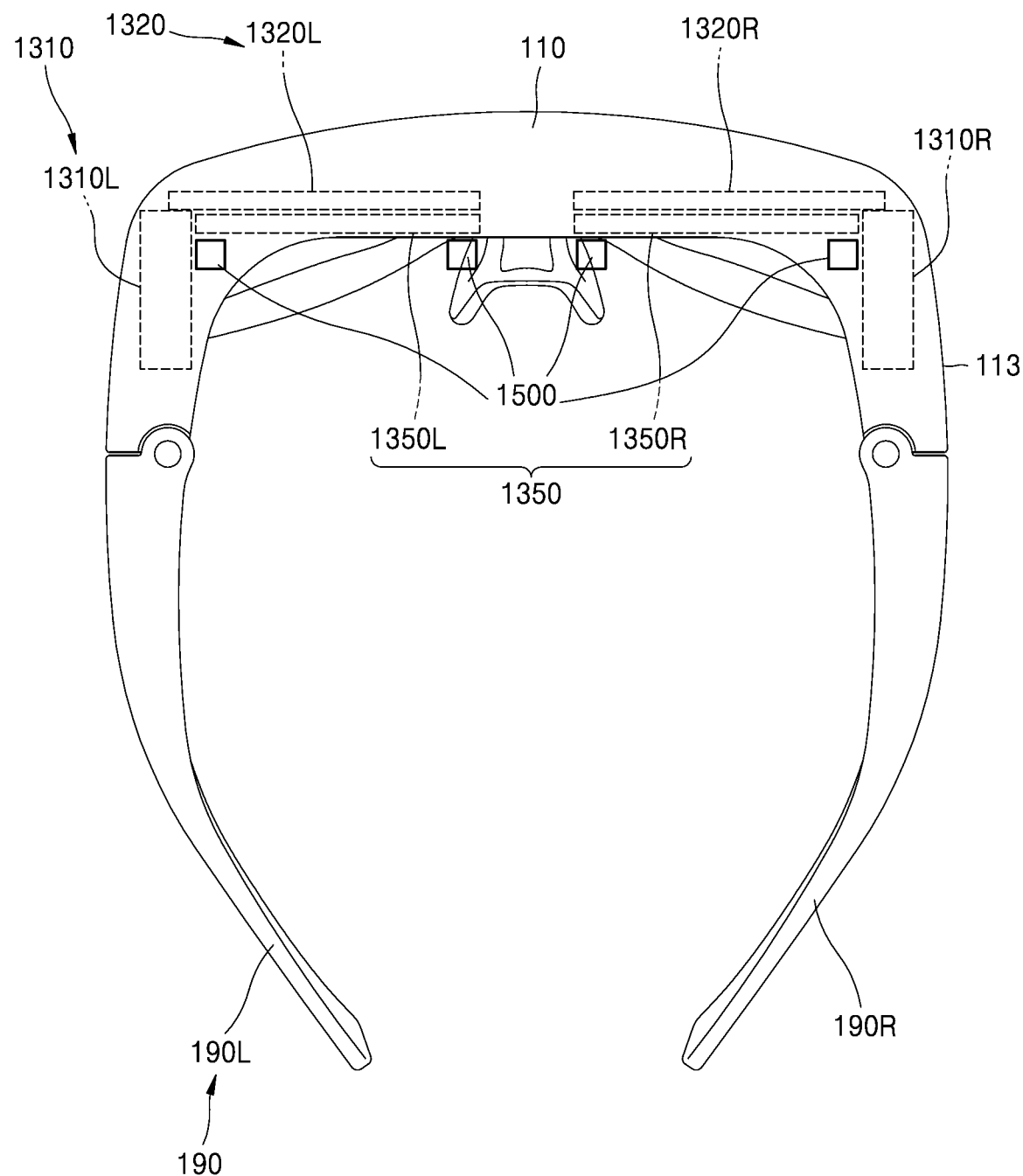
FIG. 3 is a diagram illustrating an example of an augmented reality device including a varifocal lens unit, according to an embodiment of the disclosure.

FIG. 3 is a diagram illustrating an example of the augmented reality device 1000 including the varifocal lens unit 1350, according to an embodiment of the disclosure. The augmented reality device 1000 illustrated in FIG. 2 may be implemented as, for example, but is not limited to, a glasses-type display device including a glasses-type body illustrated in FIG. 3.

Referring to FIG. 3, the augmented reality device 1000 may be a glasses-type display device, and may include a glasses-type body configured to be wearable by the user.

The glasses-type body may include a frame 110 and temples 190 including a left temple 190L and a right temple 190R, and the temples 190 may be connected to end pieces 113 of the frame 110, respectively.

In addition, the varifocal lens unit 1350 and the waveguide 1320 may be arranged at the frame 110. The varifocal lens unit 1350 may include a left-eye varifocal lens unit 1350L and a right-eye varifocal lens unit 1350R. In addition, the waveguide 1320 may be configured to receive project light at an input region, and output at least a portion of the received light at an output region. The waveguide 1320 may include a left-eye waveguide 1320L and a right-eye waveguide 1320R.

The left-eye varifocal lens unit 1350L and the left-eye waveguide 1320L may be arranged at positions corresponding to the left eye of the user, respectively, and the right-eye varifocal lens unit 1350R and the right-eye waveguide 1320R may be arranged at positions corresponding to the right eye of the user, respectively. For example, the left-eye varifocal lens unit 1350L and the left-eye waveguide 1320L may be attached to each other, or the right-eye varifocal lens unit 1350R and the right-eye waveguide 1320R may be attached to each other, but the disclosure is not limited thereto.

In addition, the optical engine 1310 to project light containing an image may include a left-eye optical engine 1310L and a right-eye optical engine 1310R. The left-eye optical engine 1310L and the right-eye optical engine 1310R may be arranged at the end pieces 113 of the frame, respectively. The light projected from the optical engine 1310 may be displayed through the waveguide 1320. Although, FIG. 3 illustrates that the optical engine 1310 may include a left-eye optical engine 1310L and a right-eye optical engine 1310R, the disclosure is not limited thereto, and as such, according to another embodiment, only one optical engine 1310 may be provided.

The gaze tracking sensor 1500 may be arranged at an edge of a lens of the augmented reality device 1000, and may include, for example, a light source module to provide light toward an eye of the user and a light sensor to receive the provided light. The light source module may provide the light toward an eye region of the user while redirecting the light at preset time intervals For example, the light (e.g., infrared (IR) light) provided from the light source module may be projected onto the eye of the user in a preset pattern (e.g., a straight line in a vertical direction or a straight line in a horizontal direction). The gaze tracking sensor 1500 may track a gaze of an eye of the user by identifying a corneal region and a pupil region of the eye of the user by using the light sensor, based on a change in the amount of light reflected from an eye region of the user.

Figure 4A:
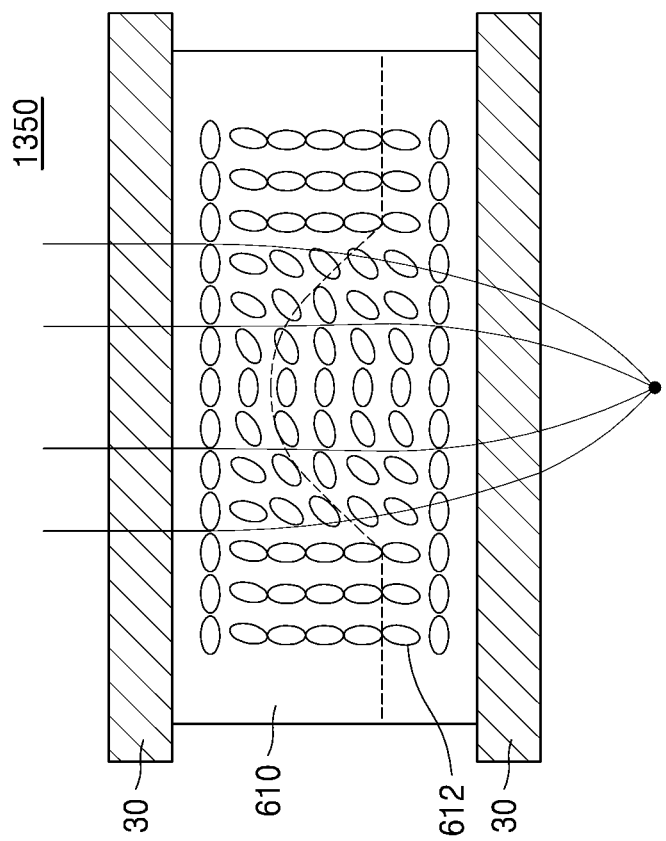
FIG. 4A is a diagram illustrating an example of adjusting the refractive power of the varifocal lens unit, according to an embodiment of the disclosure.
Figure 4A:
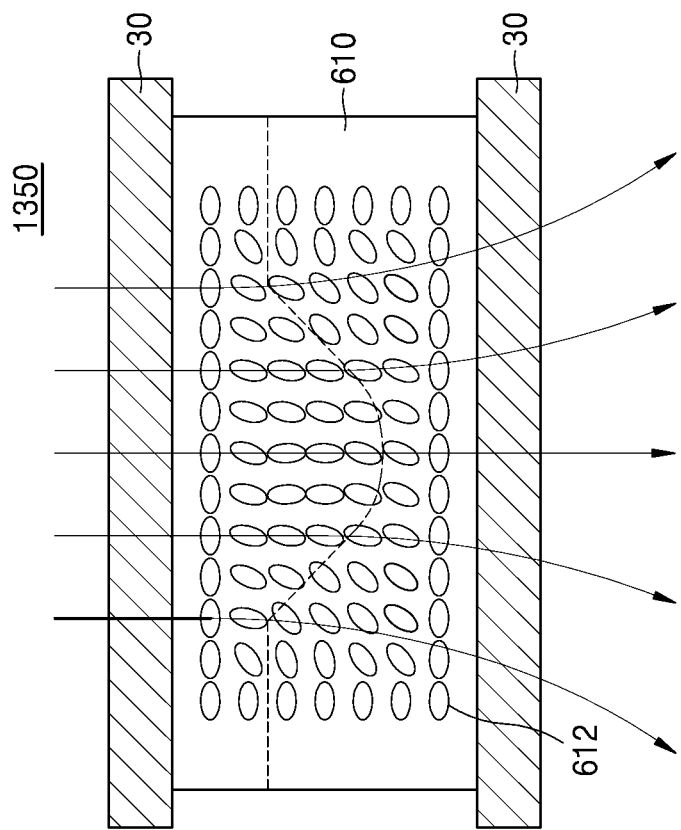

FIG. 4A is a diagram illustrating an example of adjusting the refractive power of the varifocal lens unit 1350, according to an embodiment of the disclosure.

Referring to FIG. 4A, the varifocal lens unit 1350 illustrated in FIG. 3 may be implemented to include, for example, a liquid crystal layer 610. According to an embodiment, the liquid crystal layer 610 may include liquid crystal molecules, and where the arrangement angle of the liquid crystal molecules may be changed. For example, as a control voltage modulated to have a specific phase profile is applied to electrodes 30, the arrangement angle of the liquid crystal molecules 612 arranged at a specific position in an active region of the liquid crystal layer 610 of the varifocal lens unit 1350 may be changed. As the arrangement angle of the liquid crystal molecules 612 arranged at the specific region of the liquid crystal layer 610 changes, the refractive index of light passing through the liquid crystal molecules 612 may change. When the refractive index of the light changes, the refractive power of the varifocal lens unit 1350 may change, thus the path of the light passing through the varifocal lens unit 1350 also changes, and accordingly, a vergence may change. The vergence is an index indicating a degree to which the light passing through the varifocal lens unit 1350 converges or diverges. The vergence may be adjusted according to the refractive power of the varifocal lens unit 1350.

Figure 4B:
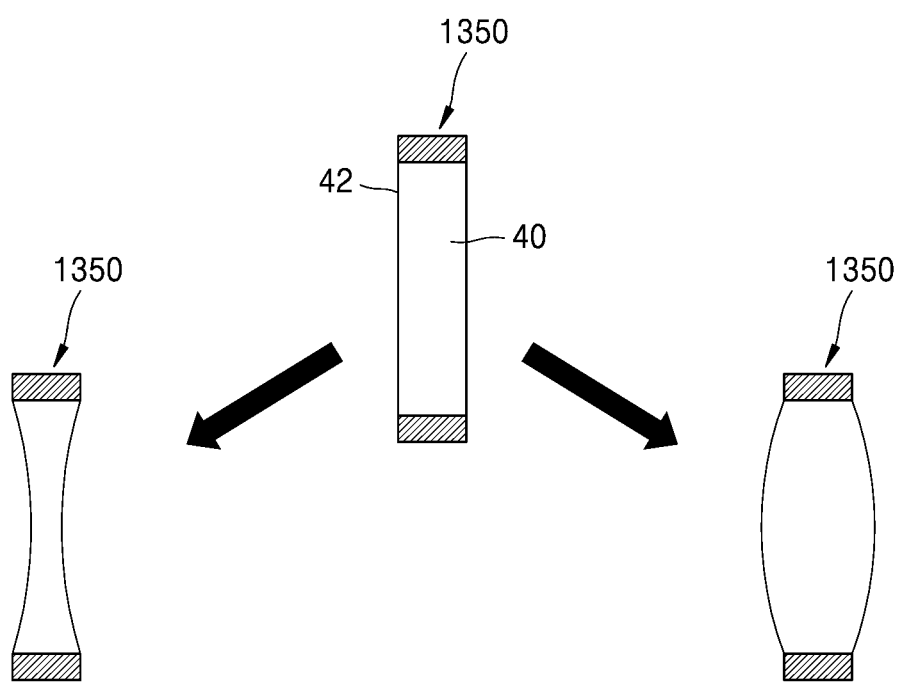
FIG. 4B is a diagram illustrating an example of adjusting the refractive power of the varifocal lens unit, according to an embodiment of the disclosure.

FIG. 4B is a diagram illustrating an example of adjusting the refractive power of the varifocal lens unit 1350, according to an embodiment of the disclosure.

Referring to FIG. 4B, the varifocal lens unit 1350 illustrated in FIG. 3 may be implemented as a liquid lens including a fluid 40 that moves according to an electrical signal. The varifocal lens unit 1350 may include the fluid 40 that moves according to an electrical signal, and a housing 42 accommodating the fluid 40. Accordingly, the augmented reality device 1000 may adjust the amount of the fluid 40 accommodated in the housing 42 of the varifocal lens unit 1350 by using an electrical signal, so as to change the configuration of the varifocal lens unit 1350 to have a configuration of a concave lens or a convex lens, and adjust the refractive power of the varifocal lens unit 1350.

An example in which the augmented reality device 1000 illustrated in FIG. 2 performs operations for the vision correction and the gaze tracking sensor calibration with respect to the user according to a correct answer rate of user inputs will be described with reference to FIGS. 5 to 7.

Figure 5:
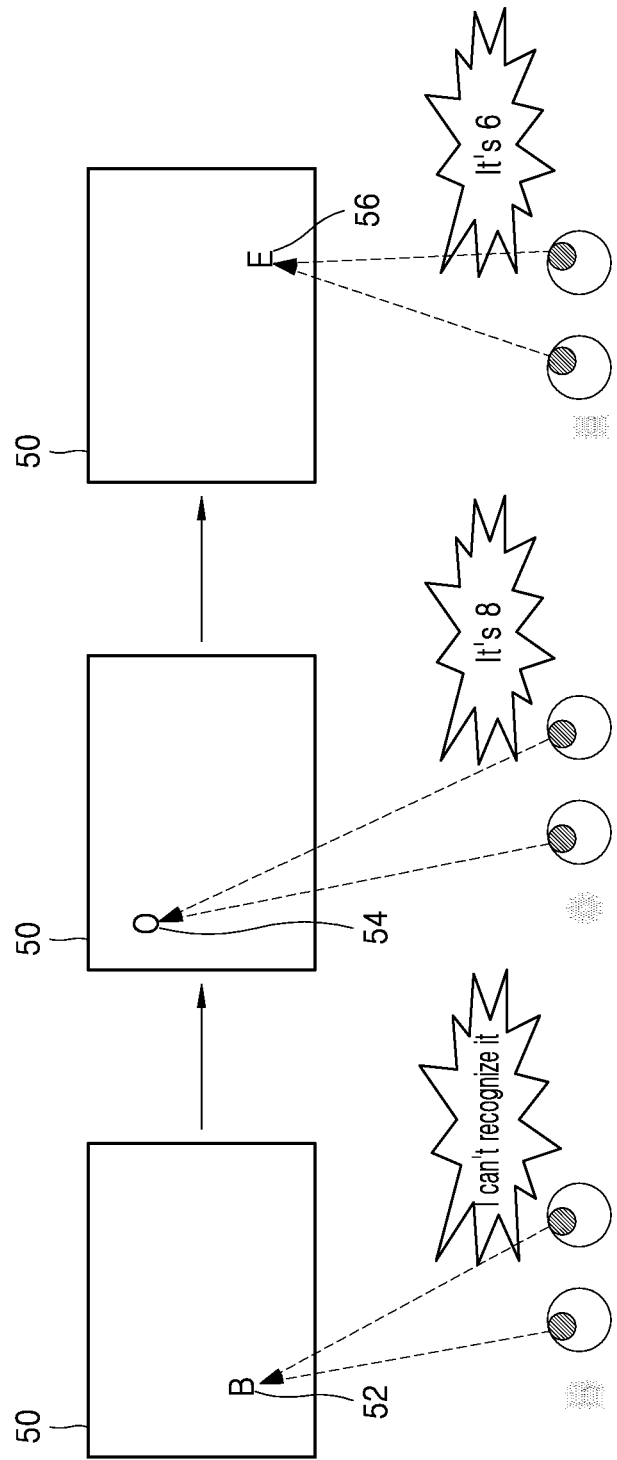
FIG. 5 is a diagram illustrating an example in which an augmented reality device performs operations for vision correction and gaze tracking sensor calibration with respect to a user in a case where a correct answer rate of user inputs is low, according to an embodiment of the disclosure.

FIG. 5 is a diagram illustrating an example in which the augmented reality device 1000 performs the operations for the vision correction and the gaze tracking sensor calibration with respect to the user in a case of the correct answer rate of the user inputs being low, according to an embodiment of the disclosure.

Referring to FIG. 5, the augmented reality device 1000 may successively display characters in a certain size with a focal length for vision measurement, and receive input from the user in response to the display characters. For instance, the augmented reality device 1000 may receive voice inputs of the user for the displayed characters. For example, the augmented reality device 1000 may successively display a character 'B' 52, a character 'O' 54, and a character 'E' 56 at different positions on a virtual vision measurement chart 50 displayed with the focal length for vision measurement. Here, as illustrated in FIG. 5, the character 'B' 52, the character 'O' 54, and the character 'E' 56 displayed on the virtual vision measurement chart 50 may appear significantly blurry to the user with poor vision. Accordingly, after displaying the character 'B' 52, the augmented reality device 1000 may receive a voice input of the user saying "I can't recognize it". In addition, thereafter, the augmented reality device 1000 may display the character 'O' 54, and receive a voice input of the user saying "It's 8". In addition, thereafter, the augmented reality device 1000 may display the character 'E' 56, and receive a voice input of the user saying "It's 6".

The augmented reality device 1000 may identify the voice input of "I can't recognize it", compare the character 'O' with a character '8', and compare the character 'E' with a character '6'. In addition, based on a result of the comparison, the augmented reality device 1000 may determine that the correct answer rate of the voice inputs of the user is 0%, and adjust the refractive power of the varifocal lens unit 1350 from '0 D' to '−2 D'. In addition, because the correct answer rate is 0%, the augmented reality device 1000 may determine that there is no gaze information to be used for the gaze tracking sensor calibration.

Although FIG. 5 illustrates an embodiment, in which, the three characters are successively displayed, and then the voice inputs of the user for the characters, and the refractive power of the varifocal lens unit 1350 is adjusted, the number of displayed characters is not limited thereto. For example, the augmented reality device 1000 may display one character, receive a voice input of the user for the character, and then determine whether the voice input of the user is correct. In addition, in a case where the user inputs an incorrect answer, the refractive power of the varifocal lens unit 1350 may be adjusted.

Figure 6:
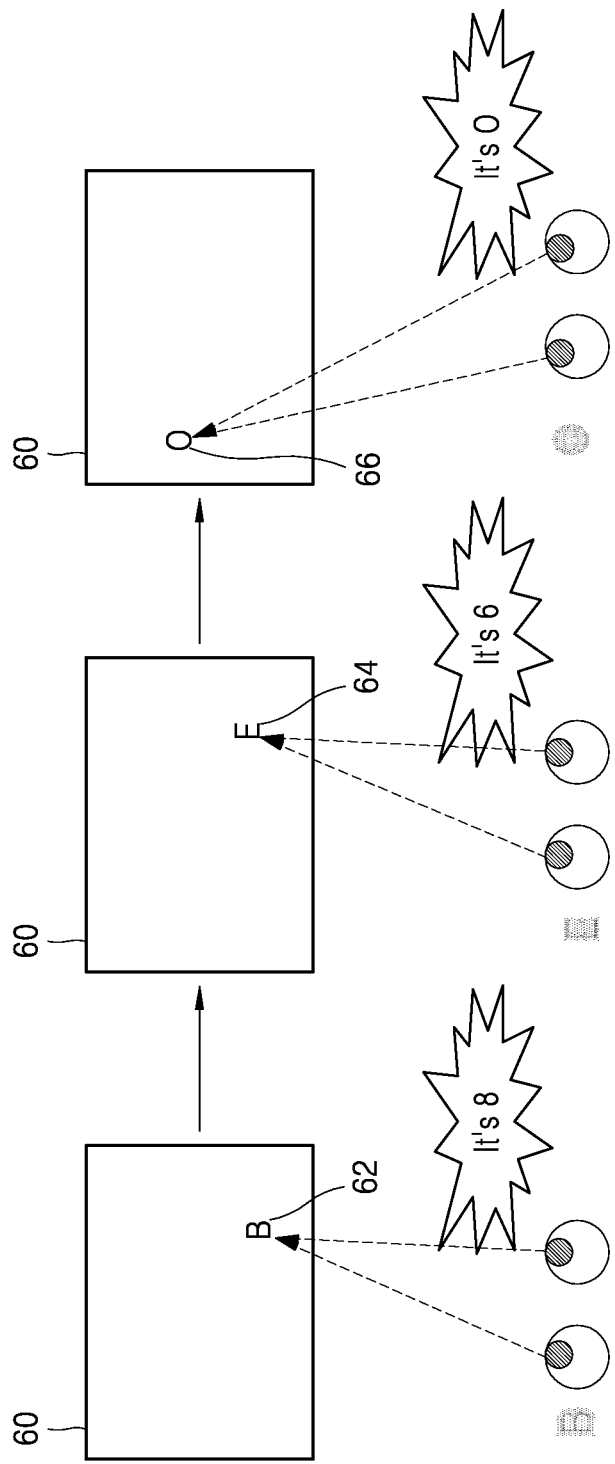
FIG. 6 is a diagram illustrating an example in which an augmented reality device performs operations for vision correction and gaze tracking sensor calibration with respect to a user in a case where a correct answer rate of user inputs is ordinary, according to an embodiment of the disclosure.

FIG. 6 is a diagram illustrating an example in which the augmented reality device 1000 performs the operations for the vision correction and the gaze tracking sensor calibration with respect to the user in a case of the correct answer rate of the user inputs being ordinary, according to an embodiment of the disclosure.

Referring to FIG. 6, after adjusting the refractive power of the varifocal lens unit 1350 to '−2 D', the augmented reality device 1000 may successively display characters in a certain size with the focal length for vision measurement, and receive voice inputs of the user for the displayed characters. For example, the augmented reality device 1000 may successively display a character 'B' 62, a character 'E' 64, and a character 'O' 66 at different positions on a virtual vision measurement chart 60 displayed with the focal length for vision measurement. In this case, the virtual vision measurement chart 60 may be the same as the virtual vision measurement chart 50. Here, as illustrated in FIG. 6, the character 'B' 62, the character 'E' 64, and the character 'O' 66 displayed on the virtual vision measurement chart 60 may appear moderately blurry to the user. Accordingly, after displaying the character 'B' 62, the augmented reality device 1000 may receive a voice input of the user saying "It's 8". In addition, thereafter, the augmented reality device 1000 may display the character 'E' 64, and receive a voice input of the user saying "It's 6". In addition, thereafter, the augmented reality device 1000 may display the character 'O' 66, and receive a voice input of the user saying "It's O".

The augmented reality device 1000 may compare the character 'B' with a voice input '8', compare the character 'E' with a voice input '6', and compare the character 'O' with a voice input 'O'. In addition, based on a result of the comparison, the augmented reality device 1000 may determine that the correct answer rate of the voice inputs of the user is 33.3%, and adjust the refractive power of the varifocal lens unit 1350 from '−2 D' to '−3 D'. In addition, because the correct answer rate is 33.3%, the augmented reality device 1000 may store the display position of the character 'O' 66 for which the user input a correct answer, and gaze information of the user at a time point at which the voice input spoken by the user to identify the character 'O' 66 is received, for the gaze tracking sensor calibration.

Although FIG. 6 illustrates an embodiment, in which, the three characters are successively displayed, and then the voice inputs of the user for the characters, and the refractive power of the varifocal lens unit 1350 is adjusted, the number of displayed characters is not limited thereto. For example, the augmented reality device 1000 may display one character, receive a voice input of the user for the character, and then determine whether the voice input of the user is correct. In addition, in a case where the user inputs an incorrect answer, the refractive power of the varifocal lens unit 1350 may be additionally adjusted.

Figure 7:
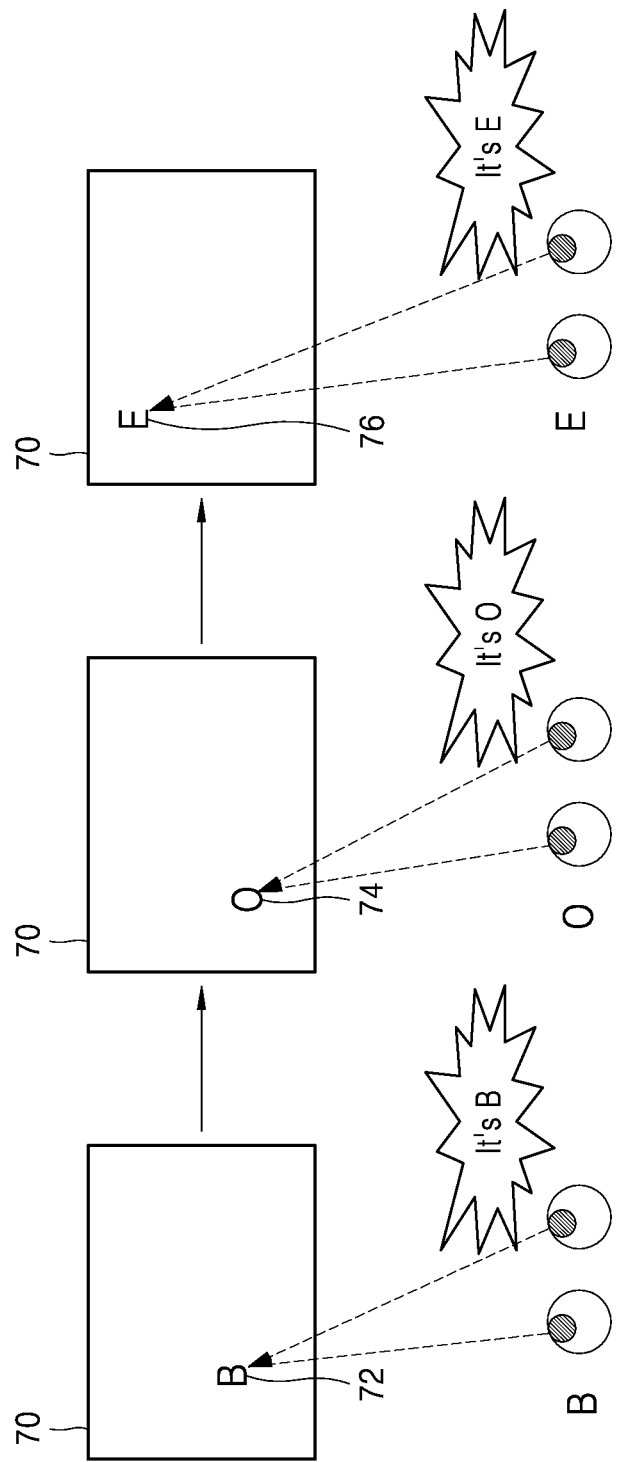
FIG. 7 is a diagram illustrating an example in which an augmented reality device performs operations for vision correction and gaze tracking sensor calibration with respect to a user in a case where a correct answer rate of user inputs is high, according to an embodiment of the disclosure.

FIG. 7 is a diagram illustrating an example in which the augmented reality device 1000 performs the operations for the vision correction and the gaze tracking sensor calibration with respect to the user in a case of the correct answer rate of the user inputs being high, according to an embodiment of the disclosure.

Referring to FIG. 7, after adjusting the refractive power of the varifocal lens unit 1350 to '−3 D', the augmented reality device 1000 may successively display characters in a certain size with the focal length for vision measurement, and receive voice inputs of the user for the displayed characters. For example, the augmented reality device 1000 may successively display a character 'B' 72, a character 'O' 74, and a character 'E' 76 at different positions on a virtual vision measurement chart 70 displayed with the focal length for vision measurement. In this case, the virtual vision measurement chart 70 may be the same as the virtual vision measurement chart 50. Here, as illustrated in FIG. 7, the character 'B' 72, the character 'O' 74, and the character 'E' 76 displayed on the virtual vision measurement chart 70 may appear sharp to the user. After displaying the character 'B' 72, the augmented reality device 1000 may receive a voice input of the user saying "It's B". In addition, thereafter, the augmented reality device 1000 may display the character 'O' 74, and receive a voice input of the user saying "It's O". In addition, thereafter, the augmented reality device 1000 may display the character 'E' 76, and receive a voice input of the user saying "It's E".

The augmented reality device 1000 may compare the character 'B' with a voice input 'B', compare the character 'O' with a voice input 'O', and compare the character 'E' with a voice input 'E'. In addition, based on a result of the comparison, the augmented reality device 1000 may determine that the correct answer rate of the voice inputs of the user is 100%, and determine the refractive power with respect to the user, to be the current refractive power of the varifocal lens unit 1350. In addition, because the correct answer rate is 100%, the augmented reality device 1000 may store, in the storage 1700, the display positions of the character 'B' 72, the character 'O' 74, and the character 'E' 76 for which the user input correct answers, and gaze information of the user at time points at which the voice inputs spoken by the user to identify the character 'B' 72, the character 'O' 74, and the character 'E' 76 are received, for the gaze tracking sensor calibration.

Although FIG. 7 illustrates an embodiment, in which, the three characters are successively displayed, and then the voice inputs of the user for the characters, and then the refractive power of the varifocal lens unit 1350 is additionally adjusted, the number of displayed characters is not limited thereto. For example, the augmented reality device 1000 may display one character, receive a voice input of the user for the character, and then determine whether the voice input of the user is correct. In addition, in a case where the user inputs a correct answer, the augmented reality device 1000 may determine the refractive power with respect to the user, to be the current refractive power of the varifocal lens unit 1350, and store the determined refractive power. According to another embodiment, in a case where the user inputs an incorrect answer, the augmented reality device 1000 may additionally adjust the refractive power of the varifocal lens unit 1350.

Thereafter, the augmented reality device 1000 may perform the gaze tracking sensor calibration with respect to the user by using data stored for the gaze tracking sensor calibration. Although FIGS. 5 to 7 illustrate that the gaze information of the user is stored for the gaze tracking sensor calibration in a case of the voice input of the user being correct, the disclosure is not limited thereto. For example, even in a case where the user inputs an incorrect answer for a displayed character, it may be considered that the user utters a voice while precisely looking at the character displayed for vision measurement, and furthermore, because the character is displayed in a size small enough to be used for the gaze tracking sensor calibration, the gaze information of the user may be stored for the gaze tracking sensor calibration even in a case of the voice input of the user being incorrect.

Although FIGS. 5 to 7 illustrate an embodiment, in which, three characters are displayed for a specific refractive power, the disclosure is not limited thereto. The number of characters to be displayed may be set differently considering whether the gaze information stored for the gaze tracking sensor calibration is sufficient. For example, in a case of the gaze information stored for the gaze tracking sensor calibration being insufficient, characters more than illustrated in FIGS. 5 to 7 may be displayed.

In addition, the refractive power of the varifocal lens unit 1350 may be adjusted by an amount different from the amounts by which the refractive powers illustrated in FIGS. 5 and 6 are adjusted. In this case, the amount by which the refractive power of the varifocal lens unit 1350 is to be adjusted may be set to vary based on the correct answer rate of the user. For example, in a case of the correct answer rate of the user being low, the augmented reality device 1000 may adjust the refractive power of the varifocal lens unit 1350 by a large amount, so as to reduce the number of times of adjusting the refractive power for vision correction of the user. For example, in a case of the correct answer rate of the user being high, the augmented reality device 1000 may adjust the refractive power of the varifocal lens unit 1350 by a small amount, so as to precisely correct the vision of the user.

Figure 8:
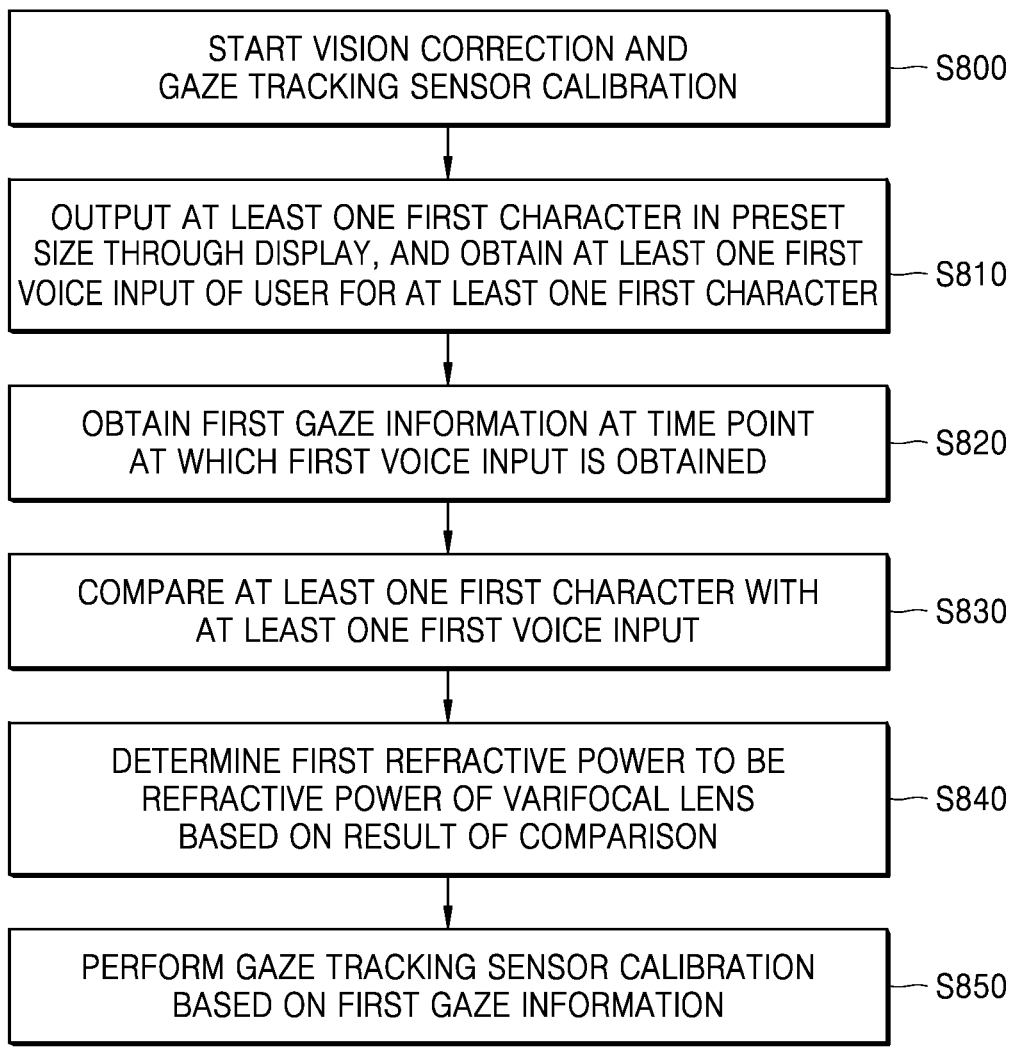
FIG. 8 is a flowchart of a method of performing gaze tracking sensor calibration with respect to a user before adjusting a refractive power of a varifocal lens unit, according to an embodiment of the disclosure.

FIG. 8 is a flowchart of a method of performing the gaze tracking sensor calibration with respect to the user before adjusting the refractive power of the varifocal lens unit 1350, according to an embodiment of the disclosure. According to an embodiment, the method illustrated in FIG. 8 is performed by the augmented reality device 1000.

In operation S800, the augmented reality device 1000 may start the vision correction and the gaze tracking sensor calibration. The processor 1800 of the augmented reality device 1000 may provide a graphical user interface (GUI) for the vision correction and the gaze tracking sensor calibration with respect to the user, in order to perform the vision correction and the gaze tracking sensor calibration with respect to the user at the same time. A virtual image of the GUI may be projected onto the waveguide 1320 from the optical engine 1310, and the virtual image of the GUI projected onto the waveguide 1320 may be reflected in the waveguide 1320 according to the principle of total reflection. The light path of the virtual image of the GUI projected onto the waveguide 1320 may be redirected by the diffraction gratings formed in the plurality of regions such that the virtual image of the GUI is finally output to the user's eyes. The vision correction with respect to the user may be an operation of determining the refractive power of the varifocal lens unit 1350 with respect to the user. The augmented reality device 1000 may start the operations for the vision correction and the gaze tracking sensor calibration according to a user input through the GUI. For example, the augmented reality device 1000 may identify the user and start the vision correction and the gaze tracking sensor calibration with respect to the identified user, based on the user input through the GUI.

In operation S810, the processor 1800 of the augmented reality device 1000 may output at least one first character in a preset size through the display 1300, and obtain at least one first voice input of the user for the at least one first character through the microphone 1200.

The processor 1800 of the augmented reality device 1000 may successively display the at least one first character in the preset size on at least one first position on the waveguide 1320, and successively receive the at least one voice input of the user for the at least one first character.

In this case, the first position at which the first character is displayed may be determined such that various pieces of gaze information of the user may be obtained with respect to a plurality of display positions that are set to be required for the gaze tracking sensor calibration. For example, preset positions on the waveguide 1320 that are required for the gaze tracking sensor calibration may be successively selected as the first position at which the first character is displayed. The positions required for the augmented reality device 1000 to perform the gaze tracking sensor calibration with respect to the user may be preset when the augmented reality device 1000 is manufactured, but the disclosure is not limited thereto.

In operation S820, the processor 1800 of the augmented reality device 1000 may obtain first gaze information at a time point at which a first voice input is obtained. The augmented reality device 1000 may obtain the first gaze information of the user at the time point at which the first voice input of the user for a first character displayed through the display 1300 is received through the microphone 1200. The gaze information of the user may be information related to a gaze of the user, and may include, for example, but is not limited to, positions of the pupils of the user, coordinates of the centers of the pupils, a gaze direction of the user, or the like. For example, the augmented reality device 1000 may monitor gaze directions of the user through the gaze tracking sensor 1500, and, when the reception of the first voice input of the user through the microphone 1200 is detected, may extract the first gaze information at the time point at which the first voice input is received, from among monitored gaze directions. In this case, for example, as a character for the gaze tracking sensor calibration is displayed on the waveguide 1320, an operation of monitoring gaze directions of the user may be started, but the disclosure is not limited thereto.

In addition, a first gaze direction of the user may be identified based on the obtained first gaze information. A gaze direction of the user at a time point at which a voice input is received may be, for example, but is not limited to, a gaze direction during a preset critical time period before and after a time point at which the reception of the voice input is detected through the microphone 1200.

In operation S830, the processor 1800 of the augmented reality device 1000 may compare at least one displayed first character with at least one first voice input. The augmented reality device 1000 may compare the at least one first character displayed through the display 1300 with at least one character corresponding to the at least one first voice input spoken by the user to identify the at least one first character. The augmented reality device 1000 may identify, from the first voice input, a character corresponding to the first voice input by using the STT function.

For example, in a case where a plurality of first characters are displayed, the processor 1800 of the augmented reality device 1000 may determine whether the plurality of first characters are identical to characters corresponding to first voice inputs spoken by the user to identify the plurality of first characters, respectively. In addition, the processor 1800 of the augmented reality device 1000 may calculate a first correct answer rate indicating how many characters corresponding to the first voice inputs spoken by the user to identify the plurality of first characters are identical to the plurality of first characters, respectively.

For example, in a case where a single first character is displayed, the processor 1800 of the augmented reality device 1000 may determine whether a character corresponding to a first voice input spoken by the user to identify the first character is identical to the first character.

In operation S840, the processor 1800 of the augmented reality device 1000 may determine a first refractive power to be the refractive power of the varifocal lens unit 1350 based on a result of the comparison of the displayed first character with the first voice input.

For example, the processor 1800 of the augmented reality device 1000 may determine the refractive power of the varifocal lens unit 1350 of the augmented reality device 1000 based on the first correct answer rate, and adjust the refractive power of the varifocal lens unit 1350. For example, in a case of the first correct answer rate being low, the refractive power of the varifocal lens unit 1350 may be adjusted by a large amount, whereas in a case of the first correct answer rate being high, the refractive power of the varifocal lens unit 1350 may be adjusted by a small amount.

According to another embodiment, for example, in a case where the processor 1800 of the augmented reality device 1000 receives a single first voice input for a single first character through the microphone 1200, and the first voice input is incorrect, the augmented reality device 1000 may adjust the refractive power of the varifocal lens unit 1350 to the first refractive power.

In addition, the processor 1800 of the augmented reality device 1000 may store the first refractive power as the refractive power of the varifocal lens unit 1350 with respect to the user. For example, the processor 1800 of the augmented reality device 1000 may store a diopter value corresponding to the first refractive power.

In operation S850, the processor 1800 of the augmented reality device 1000 may perform the gaze tracking sensor calibration with respect to the user based on the first gaze information. For example, in order to perform configuration for accurate determination of a position on the waveguide 1320 of the augmented reality device 1000 at which the user is looking, the processor 1800 of the augmented reality device 1000 may map gaze information related to a first gaze direction of the user at a time point at which a first voice input that is correct is input, with coordinate values representing a display position of a first character corresponding to the first voice input that is correct. By performing the gaze tracking sensor calibration, a point on the waveguide 1320 at which the user is actually looking, and a point on the waveguide 1320 that the augmented reality device recognizes that the user is looking at, may be identical to each other.

In a case where the vision correction and the gaze tracking sensor calibration with respect to the user are not sufficiently performed, the processor 1800 of the augmented reality device 1000 may additionally perform the operations for the vision correction and the gaze tracking sensor calibration. In a case where the vision correction and the gaze tracking sensor calibration with respect to the user are not sufficiently performed, the processor 1800 of the augmented reality device 1000 may perform operations illustrated in FIG. 9 that will be described below, without performing operation S850. An example of a case where the vision correction and the gaze tracking sensor calibration with respect to the user are not sufficiently performed may be a case where a position that is not mapped with gaze information of the user exists among the plurality of positions on the waveguide 1320 that are preset for the gaze tracking sensor calibration.

Figure 9:
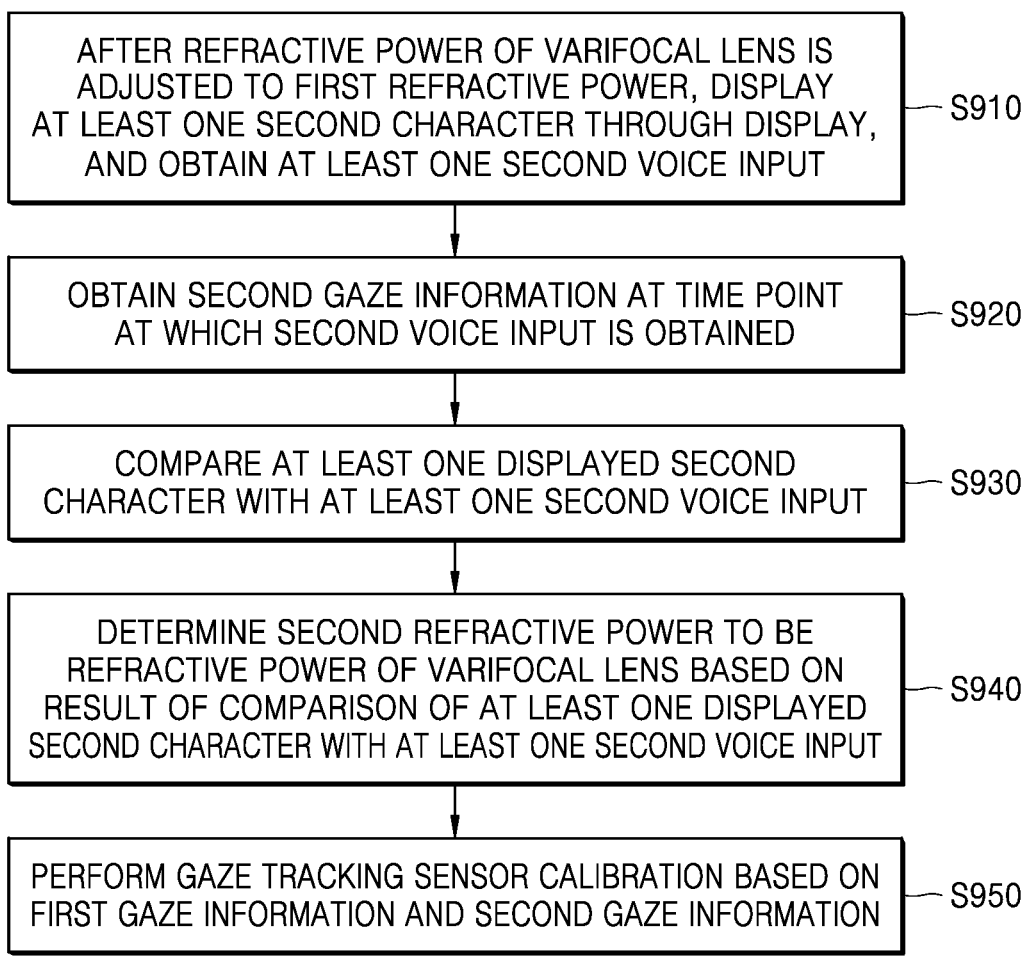
FIG. 9 is a flowchart of a method, performed by an augmented reality device, of performing gaze tracking sensor calibration with respect to a user after adjusting refractive power of a varifocal lens unit, according to an embodiment of the disclosure.

FIG. 9 is a flowchart of a method, performed by the augmented reality device 1000, of performing the gaze tracking sensor calibration with respect to the user after adjusting the refractive power of the varifocal lens unit 1350, according to an embodiment of the disclosure.

In operation S910, after the refractive power of the varifocal lens unit 1350 is adjusted to the first refractive power, the processor 1800 of the augmented reality device 1000 may display at least one second character through the display 1300, and successively receive at least one second voice input through the microphone 1200. After the refractive power of the varifocal lens unit 1350 is adjusted to the first refractive power, the processor 1800 of the augmented reality device 1000 may successively display the at least one second character at at least one second position on the waveguide 1320, and successively receive the at least one second voice input. The processor 1800 of the augmented reality device 1000 may successively display the at least one second character in a preset size at at least one second position on the waveguide 1320, and successively receive the at least one second voice input of the user for the at least one second character being displayed. The second character may be displayed on the waveguide 1320 in the same size and at the same depth as those of the first character. In addition, similar to the first position at which the first character is displayed, the second position at which the second character is displayed may be selected from among the positions required for the gaze tracking sensor calibration.

For example, the processor 1800 of the augmented reality device 1000 may display a second character that is in a certain size preset for determining the refractive power and performing the gaze tracking sensor calibration, and is randomly selected, at a preset depth for measuring the visual acuity of the user. In this case, the second position at which the second character is displayed may be determined such that various pieces of second gaze information of the user may be obtained with respect to the plurality of display positions that are preset for the gaze tracking sensor calibration. The second position at which the second character is displayed by the augmented reality device 1000 may be a position on which it is determined that calibration by the calibration module 1730 is not sufficiently performed, from among the positions on the waveguide 1320 that are preset to be required for the gaze tracking sensor calibration. For example, in a case where it is determined that a voice input spoken by the user to identify a character displayed at a specific position has been received a preset number of times, the processor 1800 of the augmented reality device 1000 may determine that the calibration has been sufficiently performed on the specific position, but the disclosure is not limited thereto.

In operation S920, the processor 1800 of the augmented reality device 1000 may obtain second gaze information at a time point at which a second voice input is obtained. The augmented reality device 1000 may obtain the second gaze information of the user at the time point at which the second voice input of the user for a second character displayed on the waveguide 1320 is received through the microphone 1200. For example, the processor 1800 of the augmented reality device 1000 may monitor gaze directions of the user through the gaze tracking sensor 1500, and, when the reception of the second voice input of the user through the microphone 1200 is detected, may extract a second gaze direction at the time point at which the second voice input is received, from among monitored gaze directions.

In operation S930, the processor 1800 of the augmented reality device 1000 may compare at least one displayed second character with at least one second voice input. The processor 1800 of the augmented reality device 1000 may identify, from the second voice input, a character corresponding to the second voice input by using the STT function. The processor 1800 of the augmented reality device 1000 may determine whether the at least one second character is identical to at least one character corresponding to at least second voice input spoken by the user to identify the at least one second character.

For example, in a case where a plurality of second characters are displayed, the processor 1800 of the augmented reality device 1000 may determine whether the plurality of second characters are identical to characters corresponding to second voice inputs spoken by the user to identify the plurality of second characters, respectively.

For example, in a case where a single second character is displayed, the processor 1800 of the augmented reality device 1000 may determine whether the second character is identical to a character corresponding to a second voice input spoken by the user to identify the second character.

In operation S940, the processor 1800 of the augmented reality device 1000 may determine a second refractive power to be the refractive power of the varifocal lens unit 1350 based on a result of the comparison of the at least one displayed second character with the at least one second voice input. In addition, the processor 1800 of the augmented reality device 1000 may store the second refractive power as the refractive power of the varifocal lens unit 1350 with respect to the user. For example, the processor 1800 of the augmented reality device 1000 may store a diopter value corresponding to the second refractive power. The processor 1800 of the augmented reality device 1000 may adjust the refractive power of the varifocal lens unit 1350 to the second refractive power.

In operation S950, the processor 1800 of the augmented reality device 1000 may perform the gaze tracking sensor calibration with respect to the user based on the first gaze information and the second gaze information. The processor 1800 of the augmented reality device 1000 may map the first gaze information at the time point at which the first voice input that is correct is input, with coordinate values representing the display position of the first character corresponding to the first voice input that is correct, and may map the second gaze information at the time point at which the second voice input that is correct is input, with coordinate values representing the display position of the second character corresponding to the second voice input that is correct.

In a case where the vision correction and the gaze tracking sensor calibration with respect to the user are not sufficiently performed, the processor 1800 of the augmented reality device 1000 may repeatedly perform the operations for the vision correction and the gaze tracking sensor calibration with respect to the user.

Meanwhile, by executing the vision calculation module 1720, the processor 1800 of the augmented reality device 1000 may calculate the visual acuity of the user. In a case of the second correct answer rate being greater than or equal to a preset threshold, the processor 1800 of the augmented reality device 1000 may determine the refractive power of the varifocal lens unit 1350. For example, in a case of the second correct answer rate being 90% or greater, the processor 1800 of the augmented reality device 1000 may determine the refractive power with respect to the user, to be the current refractive power of the varifocal lens unit 1350. According to another embodiment, for example, in a case of a voice input for a displayed character being correct, the processor 1800 of the augmented reality device 1000 may determine the refractive power with respect to the user, to be the current refractive power of the varifocal lens unit 1350.

In addition, the processor 1800 of the augmented reality device 1000 may identify a visual acuity of the user corresponding to the determined refractive power. In this case, the visual acuity of the user may be identified by using the table indicating visual acuities of the user respectively corresponding to refractive powers of a lens.

Accordingly, the augmented reality device 1000 may adjust the refractive power of the varifocal lens unit 1350 to correct the vision of the user, while efficiently performing the gaze tracking sensor calibration of the augmented reality device 1000 based on the gaze directions of the user precisely looking at the characters in a small size.

One or more embodiments of the disclosure may be implemented as a recording medium including computer-readable instructions such as a computer-executable program module. A computer-readable medium may be any available medium which is accessible by a computer, and may include a volatile or non-volatile medium and a removable or non-removable medium. Also, the computer-readable mediums may include computer storage mediums and communication mediums. The computer storage media include both volatile and non-volatile, removable and non-removable media implemented in any method or technique for storing information such as computer readable instructions, data structures, program modules or other data. The communication medium may typically include computer-readable instructions, data structures, or other data of a modulated data signal such as program modules.

A computer-readable storage medium may be provided in a form of a non-transitory storage medium. Here, the term 'non-transitory storage medium' refers to a tangible device and does not include a signal (e.g., an electromagnetic wave), and the term 'non-transitory storage medium' does not distinguish between a case where data is stored in a storage medium semi-permanently and a case where data is stored temporarily. For example, the non-transitory storage medium may include a buffer in which data is temporarily stored.

According to an embodiment of the disclosure, the method according to various embodiments disclosed herein may be included in a computer program product and provided. The computer program product may be traded between a seller and a purchaser as a commodity. The computer program product may be distributed in a form of a machine-readable storage medium (e.g., compact disk read only memory (CD-ROM)), or may be distributed online (e.g., downloaded or uploaded) through an application store (e.g., Google Play™) or directly between two user devices (e.g., smart phones). In the case of online distribution, at least a portion of the computer program product (e.g., a downloadable app) may be temporarily stored in a machine-readable storage medium such as a manufacturer's server, an application store's server, or a memory of a relay server.

In addition, in the specification, the term "unit" may be a hardware component such as a processor or a circuit, and/or a software component executed by a hardware component such as a processor.

Throughout the disclosure, the expression "include at least one of a, b or c" means "include only a", "include only b", "include only c", "include a and b", "include b and c", "include a and c", or "include a, b, and c".

The above-described description of the disclosure is provided only for illustrative purposes, and those of skill in the art will understand that the disclosure may be easily modified into other detailed configurations without modifying technical aspects and essential features of the disclosure. Therefore, it should be understood that the above-described embodiments are exemplary in all respects and are not limited. For example, the elements described as single entities may be distributed in implementation, and similarly, the elements described as distributed may be combined in implementation.

The scope of the disclosure is not defined by the detailed description of the disclosure but by the following claims, and all modifications or alternatives derived from the scope and spirit of the claims and equivalents thereof fall within the scope of the disclosure.

The invention claimed is:

1. A method of adjusting refractive power of a varifocal lens of an augmented reality device, the method comprising:
    outputting a first character having a first size at a first position on a waveguide of the augmented reality device;
    obtaining a first user input response corresponding to the first character;
    obtaining at least one piece of first gaze information detected through a gaze tracking sensor of the augmented reality device at a time point at which the first user input response is obtained;
    comparing the first character with the first user input response;
    determining, based on a result of the comparing, refractive power of the varifocal lens of the augmented reality device at the time point at which the first user input response is obtained as a first refractive power; and
    performing gaze tracking sensor calibration by mapping the at least one piece of first gaze information with coordinate values representing the first position where the first character is displayed on the waveguide.

2. The method of claim 1, further comprising:
    after the determining the first refractive power to be the refractive power of the varifocal lens, outputting a second character having the first size through the waveguide;
    obtaining a second user input response corresponding to the second character;
    obtaining at least one piece of second gaze information detected through the gaze tracking sensor based on the second user input response;
    comparing the second character with the second user input response; and
    determining a second refractive power to be the refractive power of the varifocal lens of the augmented reality device, based on a result of the comparing of the second character with the second user input response,
    wherein the performing of the gaze tracking sensor calibration is performed based on the at least one piece of first gaze information and the at least one piece of second gaze information.

3. The method of claim 2, wherein the first size of the first character and the second character corresponds to a preset corrected visual acuity, and wherein the first character and the second character are displayed at a preset depth for measuring a visual acuity of the user.

4. The method of claim 1,
    wherein the first position is at least one of a plurality of positions on the waveguide that are preset for the gaze tracking sensor calibration.

5. The method of claim 1, wherein the comparing of the first character with the first user input response comprises comparing the first character with a character included in the first user input response.

6. The method of claim 1, wherein the refractive power of the varifocal lens is adjusted by changing an arrangement of liquid crystal (LC) molecules in the varifocal lens.

7. The method of claim 1, further comprising:
    obtaining vision information of a user; and
    adjusting the refractive power of the varifocal lens of the augmented reality device in advance based on the obtained vision information,
    wherein the outputting of the first character is performed by displaying the first character after the refractive power of the varifocal lens is adjusted in advance based on the obtained vision information.

8. The method of claim 2, wherein the at least one piece of first gaze information is stored with a first display position of the first character and the at least one piece of second gaze information is stored with a second display position of the second character.

9. The method of claim 8, wherein the at least one piece of first gaze information and the at least one piece of second gaze information are obtained by at least one gaze tracking sensor arranged to track an eye of a user at the augmented reality device.

10. An augmented reality device comprising:
    a display comprising a waveguide;
    a gaze tracking sensor configured to track a gaze of a user;
    a varifocal lens;
    a memory storing one or more instructions; and
    a processor configured to execute the one or more instructions to:
        control the display to output a first character in having a first size at a first position on the waveguide,
        obtain a first user input response corresponding to the first character,
        control the gaze tracking sensor to obtain at least one piece of first gaze information detected through the gaze tracking sensor at a time point at which the first user input response is obtained,
        compare the first character with the first user input response,
        determine, based on a result of the compare operation, a refractive power of the varifocal lens at the time point at which the first user input response is obtained as a first refractive power, and
        perform gaze tracking sensor calibration by mapping the at least one piece of first gaze information with coordinate values representing the first position where the first character is displayed on the waveguide.

11. The augmented reality device of claim 10, wherein the processor is further configured to execute the one or more instructions to:
- after the first refractive power is determined to be the refractive power of the varifocal lens, output a second character having the first size,
- obtain a second user input response corresponding to the second character,
- obtain at least one piece of second gaze information detected through the gaze tracking sensor based on the second user input response,
- compare the second character with the second user input response,
- determine a second refractive power to be the refractive power of the varifocal lens, based on a result of the comparing of the second character with the second user input response, and
- perform the gaze tracking sensor calibration based on the at least one piece of first gaze information and the at least one piece of second gaze information.

12. The augmented reality device of claim 11, wherein the first size of the first character and the second character corresponds to a preset corrected visual acuity, and wherein the first character and the second character are displayed at a preset depth for measuring a visual acuity of the user.

13. A non-transitory computer-readable recording medium having recorded thereon a program for executing the method of claim 1, on a computer.

* * * * *